United States Patent
Naber et al.

(10) Patent No.: US 11,138,728 B2
(45) Date of Patent: Oct. 5, 2021

(54) COMPUTER-IMPLEMENTED METHOD, COMPUTER PROGRAM AND DIAGNOSTIC SYSTEM, IN PARTICULAR FOR DETERMINING AT LEAST ONE GEOMETRIC FEATURE OF A SECTION OF A BLOOD VESSEL

(71) Applicant: Carl Zeiss Meditec AG, Jena (DE)

(72) Inventors: Ady Naber, Karlsruhe (DE); Daniel Berwanger, Karlsruhe (DE); Werner Nahm, Buehlerzell (DE); Christoph Hauger, Aalen (DE); Roland Guckler, Ulm (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 17/166,945

(22) Filed: Feb. 3, 2021

(65) Prior Publication Data

US 2021/0241453 A1  Aug. 5, 2021

(30) Foreign Application Priority Data

Feb. 3, 2020  (DE) .................... 10 2020 102 683.8

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0071* (2013.01); *A61B 5/02007* (2013.01);
(Continued)

(58) Field of Classification Search
CPC .......... G06T 7/0012; G06T 7/62; G06T 7/68; G06T 7/149; G06T 2207/10064;
(Continued)

(56) References Cited

U.S. PATENT DOCUMENTS

| | | | |
|---|---|---|---|
| 8,229,186 B2 * | 7/2012 | Milstein | G06T 7/181 382/128 |
| 2003/0056799 A1 | 3/2003 | Young et al. | |

(Continued)

OTHER PUBLICATIONS

English and German versions of Wikipedia article "Ramer-Douglas-Peucker algorithm" English version last updated on Nov. 30, 2020, German version last updated on Jun. 26, 2019, 8 pages.
(Continued)

*Primary Examiner* — Brenda C Bernardi
(74) *Attorney, Agent, or Firm* — Walter Ottesen, P.A.

(57) ABSTRACT

A computer-implemented method determines a geometric feature of a section of a blood vessel in an operating region. An image of the section is provided. An adapted blood vessel model is provided via image processing for the section by adapting a blood vessel model, which describes the section as a flow channel with a wall delimiting the latter and with an axis of symmetry. A centerline of the section of the blood vessel is determined as a contiguous pixel line. A relative spatial position of the side of the wall is ascertained based on the centerline and the image provided. The geometric feature is derived from the adapted blood vessel model. The disclosure also relates to a method for determining the length of a contiguous pixel line in an image and a system for determining a geometric feature of a section of an object.

20 Claims, 15 Drawing Sheets

(51) Int. Cl.
  *A61B 5/02* (2006.01)
  *G06T 7/62* (2017.01)
  *G06T 7/149* (2017.01)
  *A61K 49/00* (2006.01)
  *G06T 7/68* (2017.01)

(52) U.S. Cl.
  CPC .......... *A61K 49/0017* (2013.01); *G06T 7/149* (2017.01); *G06T 7/62* (2017.01); *G06T 7/68* (2017.01); *G06T 2207/10064* (2013.01); *G06T 2207/30101* (2013.01); *G06T 2207/30172* (2013.01)

(58) Field of Classification Search
  CPC ........... G06T 2207/30101; G06T 2207/30172; A61K 49/0017; A61B 5/0071; A61B 5/02007
  See application file for complete search history.

(56) References Cited

U.S. PATENT DOCUMENTS

2015/0148662 A1  5/2015  Alex
2017/0323587 A1  11/2017  Yagi et al.

OTHER PUBLICATIONS

Golland, P. et al., "Fixed Topology Skeletons," International Conference on Computer Vision and Pattern Recognition (CVPR), IEEE, 2000, 8 pages.

Naber, A. et al., "In Silico Modelling of Blood Vessel Segmentations for Estimation of Discretization Error in Spatial Measurement and its Impact on Quantitative Fluorescence Angiography", 41st Annual International Conference of the IEEE Engineering in Medicine and Biology Society (EMBC), 2019, pp. 4787-4790.

Nakagawa, D. et al., "Wall-to-lumen ratio of intracranial arteries measured by indocyanine green angiography", Asian Journal of Neurosurgery, 2016, vol. 11, No. 4, pp. 361 to 364.

Otsu, N., "A threshold selection method from gray-level histograms", IEEE Trans. Sys. Man. Cyber. vol. 9, No. 1, 1979, pp. 882 to 886.

Suhadolnik, A. et al, "Digital Curve Length Calculation using B-Splines, Journal of Mathematical Imaging and Vision", vol. 38, 2010, pp. 132 to 138.

English translation and Office action of the German Patent Office dated Dec. 17, 2020 in German patent application 10 2020 102 683.8 on which the claim of priority is based.

* cited by examiner

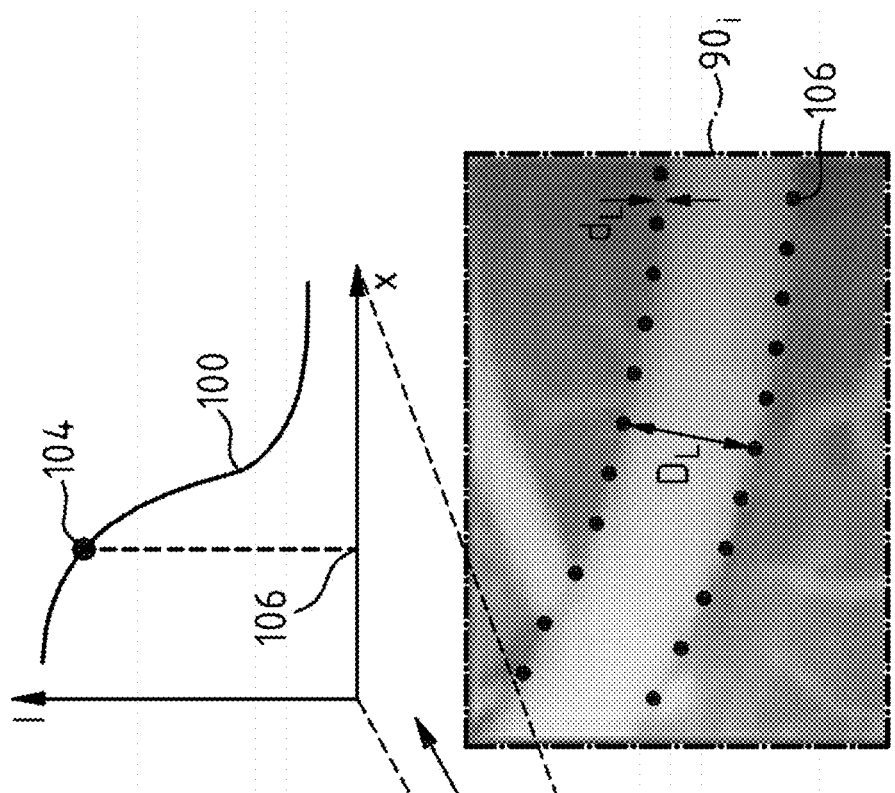

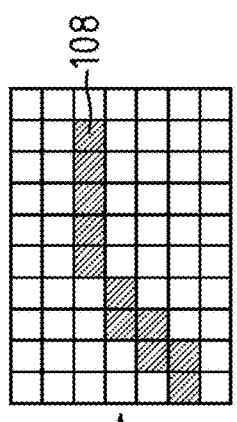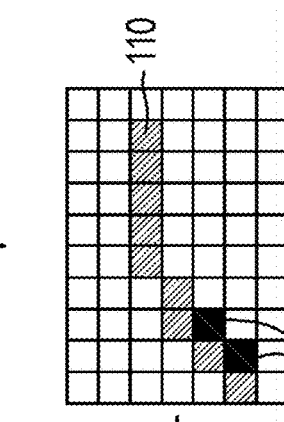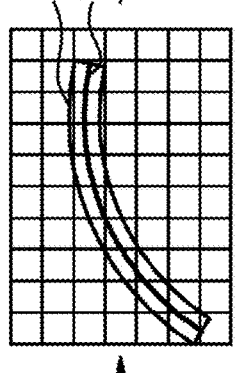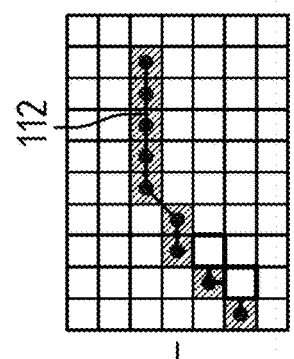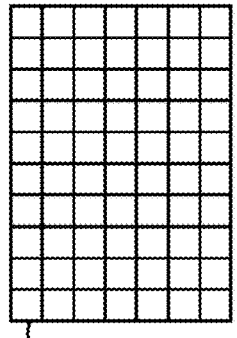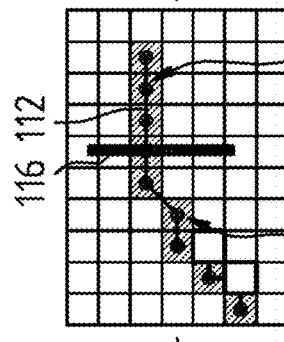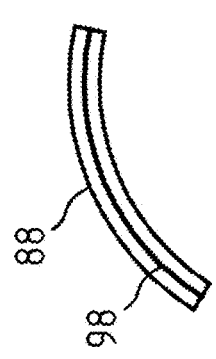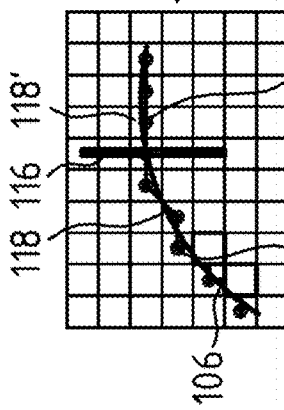

COMPUTER-IMPLEMENTED METHOD, COMPUTER PROGRAM AND DIAGNOSTIC SYSTEM, IN PARTICULAR FOR DETERMINING AT LEAST ONE GEOMETRIC FEATURE OF A SECTION OF A BLOOD VESSEL

CROSS REFERENCE TO RELATED APPLICATION

This application claims priority of German patent application no. 10 2020 102 683.8, filed Feb. 3, 2020, the entire content of which is incorporated herein by reference.

FIELD OF THE INVENTION

The disclosure relates to a computer-implemented method for determining at least one geometric feature of a section of a blood vessel in an operating region, the feature being contained in the group containing length, wall thickness, internal diameter and external diameter of the blood vessel, in which at least one image of the section of the blood vessel in the operating region is provided, in which an adapted blood vessel model is determined for the section of the blood vessel by adapting a blood vessel model, which describes the section of the blood vessel as a flow channel with a wall delimiting the latter and with an axis of symmetry, by means of image processing using at least one of the images provided, wherein a relative spatial position of the side of the wall of the section of the blood vessel which delimits the flow channel and which faces the axis of symmetry is ascertained in the at least one image provided, wherein a centerline of the section of the blood vessel in the form of a contiguous pixel line is determined in the at least one image provided from the relative spatial position of the side of the wall of the section of the blood vessel which delimits the flow channel and which faces the axis of symmetry; and wherein the at least one geometric feature of the section of the blood vessel in the operating region is derived from the adapted blood vessel model.

The invention also relates to a computer program and a diagnostic system for determining at least one geometric feature of a section of a blood vessel. Moreover, the invention relates to a computer-implemented method for determining a length of a contiguous pixel line in an image.

BACKGROUND OF THE INVENTION

The determination of geometric features such as the length or the diameter of a section of a blood vessel is of interest, for example for measuring various state parameters of a patient during surgery, for instance for measuring the blood volume flow, for a length comparison between donor and receiver blood vessels in bypass surgery and, in general, for planning surgery or identifying diseases.

Determining the length of a contiguous pixel line in an image is moreover of interest within the scope of measuring geographic features, for example, of roads or rivers in aerial images, or for measuring pixel lines in animations in a film or in computer graphics. Since the length of a pixel line is often included as a parameter in the calculation of further variables, the error propagation is minimized and the error is calculable as a result of a length determination that is as accurate as possible.

A computer-implemented method of the type set forth at the outset for determining geometric features of a section of a blood vessel is known from US 2017/0323587 A1, for example. Described therein is a method for determining a blood vessel model, in which images in respect of a blood vessel are captured and a blood vessel model is derived from the images in order then for geometric features to be determined from the blood vessel model.

US 2003/0056799 A1 specifies modeling of blood vessels by means of hollow cylinder segments.

US 2015/0148662 A1 describes the ascertainment of the blood speed between two points in a blood vessel by virtue of, in particular, the length of the blood vessel being determined and a centerline in the form of a skeleton of the blood vessel being specified. The sum of the distances of the pixels along this centerline then corresponds to the length of the blood vessel. A wall of the blood vessel with a possibly varying thickness is not taken into account therein.

The publication Naber, A., Berwanger, D. and Nahm, W., "In Silico Modelling of Blood Vessel Segmentations for Estimation of Discretization Error in Spatial Measurement and Its Impact on Quantitative Fluorescence Angiography," 41st Annual International Conference of the IEEE Engineering in Medicine and Biology Society (EMBC), 2019, pp. 4787-4790, explains as the result of simulations that such length measurement methods, which ascertain the sum of the distances of the pixels along a line as the length thereof, have on average an error of 6.3% on account of discretization errors.

A method for determining the length of a digital curve is known from the publication Suhadolnik A., Petrisic, J. and Kosel, F., "Digital Curve Length Calculation using B-spline," Journal of Mathematical Imaging and Vision, volume 38, pp. 132-138, 2010. Therein, the length of a digital curve is determined by virtue of the latter being decomposed into sections, to which B-splines are fitted.

The use of the so-called Douglas-Peucker algorithm for smoothing curves is known; a curve is decomposed into a plurality of segments therein and post-processed on the basis of pixel sequences (https://de.wikipedia.org/wiki/Douglas-Peucker-Algorithmus).

SUMMARY OF THE INVENTION

It is an object of the invention to facilitate a determination of at least one geometric feature of a section of a blood vessel in an operating region, which determination is as simple and accurate as possible.

This object can, for example, be achieved by via a method for determining at least one geometric feature of a section of a blood vessel and a method for determining the length of a contiguous pixel line.

The object can, for example, also be achieved via a computer program and via a diagnostic system according to the disclosure.

Here, geometric features denote features of the geometry of an object, in particular of a blood vessel, and originate from the group including length, wall thickness, internal diameter and external diameter of the section of the blood vessel.

A computer-implemented method for determining at least one geometric feature of a section of a blood vessel in an operating region includes the following method steps.

At least one image of the section of the blood vessel in the operating region is provided. An adapted blood vessel model is determined for the section of the blood vessel by adapting a blood vessel model, which describes the section of the blood vessel as a flow channel with a wall delimiting the latter and with an axis of symmetry, via image processing using at least one of the images provided. In the process, a relative spatial position of the side of the wall of the section of the blood vessel which delimits the flow channel and which faces the axis of symmetry is ascertained in the at least one image provided. A centerline of the section of the blood vessel in the form of a contiguous pixel line is determined from the relative spatial position of the side of the wall which delimits the flow channel and which faces the axis of symmetry in the at least one image provided. Finally, at least one geometric feature of the section of the blood vessel in the operating region is derived from the adapted blood vessel model, wherein there is post-processing of the centerline by adapting connecting structures of the pixels along the contiguous pixel line on the basis of the pixel neighborhoods thereof, wherein the post-processed centerline is decomposed into a plurality of contiguous segments on the basis of a criterion and wherein a parametric continuous function is respectively fitted to each of the plurality of segments of the post-processed centerline by adapting the function parameters such that the overall curve formed from the fitted parametric continuous functions is C1-continuous at each point.

A method according to the disclosure facilitates a determination of the geometric features of the section of the blood vessel that is as simple and accurate as possible since the blood vessel model represents the blood vessel as a flow channel with a wall surrounding the latter. By taking into account the wall of the blood vessel, the blood vessel model is realistic and as a result facilitates a more accurate ascertainment of the geometric features of the section of the blood vessel. Thus, it is possible, for example, to ascertain an external diameter of the blood vessel in the form of the overall diameter from one external wall side to the other external wall side, an internal diameter of the blood vessel in the form of the diameter of the flow channel and a wall thickness of the blood vessel. Accurately determining the geometric features of the section of the blood vessel is a precondition for an accurate determination of patient data such as, for example, the blood volume flow or the wall-to-lumen ratio (WLR), which can serve to diagnose diseases or monitor the patient during surgery or plan surgery.

It is advantageous if the blood vessel model is formed as a hollow cylinder with an axis of symmetry and a wall with a wall thickness. This simplifies the blood vessel model and consequently also the calculation of the geometric features, as a result of which it is possible to save calculation time.

To determine geometric features of the section of the blood vessel, a relative spatial position of the side of the wall of the section of the blood vessel which delimits the flow channel and which faces the axis of symmetry is determined in the at least one image provided.

It is advantageous here if the relative spatial position of the side of the wall of the section of the blood vessel which delimits the flow channel and which faces the axis of symmetry is ascertained in the at least one image provided from a segmentation of the section of the blood vessel in the at least one image provided, for example by means of image processing. This ensures an automated determination of the relative spatial position of the side of the wall of the section of the blood vessel which delimits the flow channel and which faces the axis of symmetry, and so as little interaction as possible, or even no interaction at all, with the surgeon is required during the method for determining the geometric features of the section of the blood vessel.

To this end, the section of the blood vessel is ascertained first on the basis of an image segmentation method in the at least one image provided. Here, a segmentation denotes an image which specifies a class to which the pixel belongs for each pixel. In particular, the segmentation is a binary image, where the value 1 means that the pixel belongs to the section of the blood vessel and the value 0 means that the pixel does not belong to the section of the blood vessel. To ensure a short calculation time, in particular adaptive thresholding methods, as described in, for example, the publication Nobuyuki Otsu, "A Threshold Selection Method from Gray-Level Histograms," IEEE Trans. Sys. Man. Cyber. 1979, volume 9, no. 1, pp. 62-66, which is herewith referred to in its entirety and the disclosure of which is incorporated in the description of this invention, are suitable as segmentation methods.

Other segmentation methods known to a person skilled in the art from the literature, in particular methods for segmenting blood vessels in medical images, can also be used instead of these methods. The surgeon can adapt the segmentation and/or select the section of the blood vessel in which the at least one geometric feature should be measured. The use of an image segmentation method is advantageous in that the method can run as automatically as possible, without effort on the part of the surgeon. As a result, it is also suitable, in particular, for use during surgery.

It is particularly advantageous here if the at least one image provided is based on fluorescence light in the form of light with wavelengths lying within a fluorescence spectrum of a fluorophore flowing through the section of the blood vessel. By way of example, indocyanine green (ICG) is a suitable fluorophore in this case. This is because, since the ICG fluorescence signal is used for measuring the intravascular blood volume flow in particular, the inventors have identified that the ICG contrast can also be used to determine, with an accuracy that is as high as possible, a relative spatial position of the side of the wall which delimits the flow channel and which faces the axis of symmetry.

To this end, it is therefore advantageous to ascertain a selected image from the images provided on the basis of a criterion in relation to the image brightness of the individual picture elements of the image, that is, the intensity of the picture elements, as a measure for the intensity of the diffusely reflected light captured by means of the image capturing device. This is because this criterion corresponds to a state in which the blood vessel in the image is maximally filled with the fluorescence agent and therefore the blood vessel can be identified to the best possible extent. This measure increases the accuracy when determining the relative position of the side of the wall of the section of the blood vessel which delimits the flow channel and which faces the axis of symmetry and hence also increases the accuracy when determining the geometric features of the section of the blood vessel.

However, since the fluorescence photons are scattered by the vessel wall tissue, the fluorescence contrast typically reduces in the direction of the outer vessel diameter. Hence, the relative spatial position of the side of the wall which delimits the flow channel and which faces the axis of symmetry cannot simply and automatically be derived from the fluorescence boundary and hence from the segmentation of the section of the blood vessel, for example; instead, it is necessary to take account of the intensity profile to the external wall of the blood vessel. Ascertaining the side of the wall of the section of the blood vessel which delimits the flow channel of the adapted blood vessel model and which faces the axis of symmetry on the basis of a criterion relating to a curve of the intensity profile orthogonal to the section of the blood vessel in the at least one image provided in order to develop an accurate and reliable process for determining geometric features of a section of a blood vessel is thus an insight of the invention. In this case, the curve of the intensity profile orthogonal to the section of the blood vessel can be ascertained from the segmentation of the section of the blood vessel by virtue of the edge pixels that form the edge of the segmentation being determined. Here, an edge pixel of a segmentation is defined as a pixel which has a value of 1 itself and at least one 8-connected neighboring pixel with a value of 0. The gradient of the segmentation at the edge pixels is ascertained in addition to these edge pixels. This is because the gradient points in the direction of the steepest ascent of the segmentation—that is, from 0 to 1—and hence corresponds to a direction orthogonal to the section of the blood vessel.

Here, it is particularly advantageous if the criterion in relation to the curve of the intensity profile takes account of the curvature of the curve of the intensity profile orthogonal to the section of the blood vessel in the at least one image ($80_1$, $80_2$, $80_3$, $80_4$, . . . ) provided.

The motivation for this criterion is that the inventors used a surgical microscope to record images of a material with a known wall thickness, in this case a silicone tube, filled with a blood-like medium and ICG dye and examined the intensity profile orthogonal to the edge of the silicone tube in the captured images. This was repeated for various diameters of the silicone tube and different arrangements of same under the surgical microscope. In the process, the inventors determined that, in particular, the curvature of the intensity profile orthogonal to the edge of the silicone tube in the captured images is suitable as a criterion for determining the diameter of the flow channel. Here, the curvature of the intensity profile is ascertained in the form of the second derivative of the intensity profile. In this procedure, the relative spatial position of the side of the wall of the section of the blood vessel which delimits the flow channel and which faces the axis of symmetry corresponds to those points at which the curvature of the intensity profile, when considered from the centerline to the outside, reaches a minimum.

It is therefore a discovery of the invention that points on the side of the wall of the section of the blood vessel which delimits the flow channel and which faces the axis of symmetry in each case correspond to a minimum of the curvature of the intensity profile orthogonal to the edge of the section of the blood vessel. If these so-called flow channel edge points are connected, the relative spatial position of the side of the wall which delimits the flow channel and which faces the axis of symmetry is obtained in the at least one image provided. The area bounded by the flow channel edge points then corresponds to a segmentation of the flow channel.

In addition to the spatial position of the side of the wall of the section of the blood vessel which delimits the flow channel and which faces the axis of symmetry, a centerline of the section of the blood vessel is additionally ascertained from the relative spatial position of the side of the wall of the section of the blood vessel which delimits the flow channel and which faces the axis of symmetry in the at least one image provided.

The centerline forms a central axis of the section of the blood vessel, and so the distance from the side of the wall which delimits the flow channel and which faces the axis of symmetry is the same at each point along the centerline. Under the assumption that the wall thickness does not vary along the section of the blood vessel, it also holds true for the external wall of the section of the blood vessel that the distance of the centerline from the external wall is the same at each point along the centerline.

To determine the centerline on the basis of the relative spatial position of the side of the wall of the section of the blood vessel which delimits the flow channel and which faces the axis of symmetry, pixels on the central axis of the section of the blood vessel are preferably ascertained in a first step by processing the images provided, in particular by segmenting the flow channel. To this end, it is possible to apply morphological operations such as the so-called erosion or so-called Voronoi diagrams or else other algorithms to the at least one segmented image, for example a skeletonization algorithm as described in the article "Fixed Topology Skeletons," P. Golland, W. Grimson, International Conference on Computer Vision and Pattern Recognition (CVPR), 2000, which is herewith referred to in its entirety and the disclosure of which is incorporated in the description of this invention. In this way, it is possible to ascertain a centerline of the section of the blood vessel from the segmentation of the flow channel.

Preferably, a start point and an end point of the section are also ascertained automatically in addition to the centerline in order to determine the section of the blood vessel. In this case, the start point lies in a range between 5% and 15%, preferably at 10%, of the overall length of the section of the selected blood vessel and the end point lies in a range between 80% and 95%, preferably at 90%, of the overall length of the section of the blood vessel. This avoids inaccuracies when determining the centerline, for example, by the erosion of the segmentation, which occur especially at the start and end of a section of a blood vessel, and hence the accuracy of the method is increased. In this case, the start point and the end point can be determined automatically on the basis of the centerline and the specified ranges, or they can be set by a surgeon in the selected image.

A geometric feature of the section of the blood vessel in the form of the length thereof can be determined from the ascertained centerline with the start point and the end point. In this case, the length can be determined in various ways. A simple process for ascertaining the length of the centerline lies in the determination of the sum of the Euclidean distances from pixel to pixel between start point and end point. In this process, there are errors associated with measuring the length on account of discretization errors which, on the basis of experiments, are 6.3% on average, as described in the article A. Naber, D. Berwanger, W. Nahm, "In Silico Modelling of Blood Vessel Segmentations for Estimation of Discretization Error in Spatial Measurement and its Impact on Quantitative Fluorescence Angiography," 41st Annual International Conference of the IEEE Engineering in Medicine and Biology Society (EMBC), 2019. Therefore, the length of the centerline is preferably determined by virtue of using the method for determining a length of a contiguous pixel line in an image, as described below. This is because this method facilitates a particularly accurate, simple and fast determination of the length of the centerline.

It is moreover advantageous if the relative spatial position of the external wall of the blood vessel (88) is ascertained on the basis of a segmentation (96) of the section ($90_1$, $90_2$, $90_3$, . . . ) of the blood vessel (88) in the at least one image ($80_1$, $80_2$, $80_3$, $80_4$, . . . ) provided. To this end, it is possible to ascertain, for example, a segmentation of the section of the blood vessel from an RGB image of the operating region which shows the same section of the blood vessel. Alternatively, it is also possible to adapt the parameters of the segmentation method for the segmentation of the section of the blood vessel such that the external wall of the section of the blood vessel is ascertained instead of the relative spatial position of the side of the wall of the section of the blood vessel which delimits the flow channel and which faces the axis of symmetry.

Preferably, information items about a known ratio of the internal diameter D and the external diameter G of a human blood vessel are used when ascertaining the relative spatial position of the side of the wall which delimits the flow channel and which faces the axis of symmetry and/or the external wall of the section of the blood vessel in the at least one image provided. The difference between external diameter G and internal diameter D in a human blood vessel corresponds to twice the wall thickness d. As described in Nakagawa, D. et al., Wall-to-lumen ratio of intracranial arteries measured by indocyanine green angiography," Asian Journal of Neurosurgery, 2016, volume 11, no. 4, pp. 361-364, an average human arterial wall has a normally distributed so-called wall-to-lumen ratio (WLR) of $$WLR := \frac{G-D}{2D} = \frac{d}{D} = 0.086 \pm 0.022,$$

where the mean value is 0.086 and the standard deviation is 0.022. This information item can be used to ascertain outliers, either in the points of the external wall of the blood vessel or in the flow channel edge points, by virtue of local WLR values outside of the confidence interval in relation to a set level of significance, for example, 1%, being marked as erroneous. These local measured values can be ignored when ascertaining geometric features of the section of the blood vessel which are determined by averaging of local geometric features—for example, the internal diameter, external diameter or the wall thickness. An advantage of this measure is that these geometric features can be ascertained with a greater accuracy.

In addition to the length of the section of the blood vessel, the external diameter of the section of the blood vessel can also be determined as a geometric feature of the section of the blood vessel. In this case, the assumption is made that the blood vessel model has a circular cross-section. Proceeding from points on the centerline, a circle is determined about the respective point in each case and the radius thereof is increased until the edge of the circle corresponds to the external wall of the section of the blood vessel. The mean value of the diameters of the individual circles along the centerline then corresponds to the external diameter of the blood vessel model.

In addition to the length and the external diameter of the section of the blood vessel, the internal diameter of the section of the blood vessel can also be determined as a geometric feature of the section of the blood vessel. Proceeding from points on the centerline, a circle is determined about the respective point in each case and the radius thereof is increased until the edge of the circle corresponds to the side of the wall of the section of the blood vessel which delimits the flow channel and which faces the axis of symmetry. The mean value of the diameters of the individual circles along the centerline then corresponds to the diameter of the flow channel of the blood vessel model, that is, the internal diameter thereof.

In addition to the length, the internal diameter and the external diameter of the section of the blood vessel, the wall thickness of the section of the blood vessel can also be determined as a geometric feature of the section of the blood vessel. Proceeding from points on the centerline, a circle is determined about the respective point in each case by virtue of the radius thereof being increased until the edge of the circle corresponds to the side of the wall of the section of the blood vessel which delimits the flow channel and which faces the axis of symmetry. A further circle is determined about the same point by virtue of the radius of the circle being increased until the circle edge corresponds to the external wall of the section of the blood vessel. The difference of the two radii then corresponds to the local wall thickness. The mean value of the values of the local wall thickness along the centerline then corresponds to the wall thickness of the section of the blood vessel model.

Adapting the blood vessel model to at least one image provided, by way of determining the relative position of the side of the wall which delimits the flow channel and which faces the axis of symmetry and of the centerline, can be implemented on the basis of a single image provided, in particular on the basis of an image selected on the basis of a criterion, as is described above for fluorescence light images, for example. However, it is also possible to use a plurality of images for adapting the blood vessel model. Suitable to this end, in particular, are images which are recorded at different recording times, images which are captured under different conditions, images which are captured by different modalities, for example, MRI, CT or ultrasound, or images which as an image stack image so-called slices of a volume image and consequently show the section of the blood vessel at different depths. If a plurality of images are used, the geometric features can be determined with greater accuracy since the different information items from different images can be combined by calculation. By way of example, the geometric features can be determined separately in each image and the result can subsequently be averaged.

The centerline is formed as a contiguous pixel line in the at least one image provided. Preferably, the centerline is post-processed by adapting connecting structures of the pixels along the contiguous pixel line on the basis of the pixel neighborhoods thereof, for example, the 8-connected pixel neighborhood. In particular, the number of possible connecting structures along the contiguous pixel line is reduced by virtue of removing pixels therefrom. An advantage of this measure is that discretization errors are compensated by the removal of superfluous pixels.

Particularly preferably, the adaptation of connecting structures of the pixels along the contiguous pixel line on the basis of the pixel neighborhood thereof can include the following two steps:

detecting pixel groups with in each case three successive pixels along the contiguous pixel line, wherein one pixel in each pixel group is a directly neighboring pixel of the other two pixels of the pixel group and wherein the pixels of the pixel groups define a right triangle;

removing the pixel lying opposite the base of the right triangle from each pixel group.

This post-processing causes "L"-shaped structures made of three pixels and all rotations thereof to be removed from the contiguous pixel line and to be replaced by shorter connections in the form of diagonals. An advantage of this post-processing of the contiguous pixel line is that only a specific set of connecting structures can occur along the contiguous pixel line. This results in, firstly, a particularly simple representation of the contiguous pixel line and, secondly, the ascertainment of a slightly shortened contiguous pixel line, which compensates discretization errors, by a removal of superfluous pixels from the contiguous pixel line. Since each pixel of the contiguous pixel line—apart from the start point and the end point of the contiguous pixel line—has exactly two neighboring pixels, a sort of the contiguous pixel line by a traversal of same from its start point to its end point can be ascertained directly from the post-processed contiguous pixel line.

Further preferably, the post-processed centerline in the form of the post-processed contiguous pixel line is decomposed into a plurality of contiguous segments on the basis of a criterion. An advantage thereof is that each segment of the contiguous pixel line can be approximated individually by a continuous function. This allows a particularly simple approximation of the contiguous pixel line, for example, by parametric continuous functions of particularly low degree or by continuous functions of low complexity. This avoids overfitting of the approximated curve to the contiguous pixel line, which contributes to reduction of discretization errors and, as a result, increases the accuracy of the approximation and a subsequent determination of length.

Preferably, the collinearity of in each case three successive pixels of the contiguous pixel line is taken into account in the process as a criterion for the decomposition of the post-processed contiguous pixel line into segments. Three successive pixels of the post-processed contiguous pixel line are collinear if the centers of these three pixels lie along one line. By way of example, the post-processed contiguous pixel line can be decomposed into segments in such a way that it is traversed from its start point to its end point and segment boundaries are set in each case at the middle pixel of three collinear pixels in each case. A minimum number of pixels in a segment can also be taken into account in this case. Since Bézier curves have, for example, at least four control points, it is expedient in this case to set the minimum segment length to four pixels and to set the pixel at which the segment boundary is present as the end point of the previous segment and the start point of the subsequent segment. Taking account of the collinearity of three successive pixels in each case within the scope of the decomposition of the post-processed contiguous pixel line into segments is advantageous in that it facilitates, in a particularly simple manner, a C1-continuity, that is, continuous differentiability, of the overall curve formed from the functions which approximate the individual segments. This is because this is the case when the approximating continuous function interpolates the center of the first and last pixel of a segment, as is the case for Bézier curves or B-splines, for example.

According to the disclosure, a parametric continuous function is respectively fitted to each of the plurality of segments of the centerline in the form of the post-processed contiguous pixel line by adapting the function parameters such that the overall curve formed from the fitted continuous functions is C1-continuous at each point. An advantage thereof is that the contiguous pixel line is approximated by a continuous C1-continuous overall curve, which compensates discretization errors. Moreover, the continuous differentiability of the overall curve ensures that the overall curve approximates the contiguous pixel line as accurately as possible since curves occurring in nature, such as centerlines of blood vessels, for example, are generally likewise continuously differentiable. Thus, the contiguous pixel line is approximated as realistically as possible by this measure.

In this case, it is advantageous, in particular, if the parametric continuous functions fitted to the individual segments of the post-processed contiguous pixel line are formed as Bézier curves b(x). Bézier curves b(x) are linear combinations of Bernstein polynomials $B_i^n(x)$:

$$b(x) = \sum_{i=0}^{n} b_i \cdot B_i^n(x)$$

with $$B_i^n(x) = \binom{n}{i} x^i (1-x)^{n-i}, \ 0 \le i \le n,$$

where $b_i$ represent the control points of the Bézier curve and $$\binom{n}{i}$$

denotes the binomial coefficient. Here, the degree n of the Bézier curve corresponds to the number of control points. The first and last control point are interpolated by the Bézier curve. Bézier curves are advantageous in that they can be calculated particularly easily and quickly. This also applies to the derivatives of the Bézier curves $$b'(x) = n \sum_{i=0}^{n-1} (b_{i+1} - b_i) \cdot B_i^{n-1}(x),$$

which are ascertained from differences of the control points.

Preferably, the control points of the Bézier curves approximating the individual segments of the post-processed contiguous pixel line correspond in each of the plurality of segments of the contiguous pixel line to the pixel centers of the pixels of the contiguous pixel line in this segment. As a result, the centers of the first and last pixel of a segment are interpolated by the Bézier curve in each case. Since the segment boundaries are formed by three collinear pixels in each case, the overall curve is C1-continuous. This is because the derivative of the Bézier curves is formed by the differences of successive control points, and so the derivative of the Bézier curve at the end of one segment corresponds to the derivative of the Bézier curve of the subsequent segment. The measure that the control points directly correspond to the pixel centers facilitates, firstly, a particularly simple and computation time-saving calculation of the individual Bézier curves. Secondly, this measure reduces discretization errors since the Bézier curves do not interpolate the control points except for at the start and end of the segment but instead extend within the convex envelope of the control points. As a result, the length of the Bézier curves in the individual segments is shorter than an exact interpolation of the individual pixel centers.

As an alternative to Bézier curves, B-splines can also be used as parametric continuous functions. These are advantageous in that the degree of the B-splines can be chosen independently of the number of control points, and so overfitting of the B-splines to the pixels as a result of choosing a rather low degree, for example, in the form of cubic B-splines, can be avoided. Bézier curves are advantageous over B-splines in that they can be calculated more easily and quickly and require a smaller number of basis polynomials for the approximation.

The approximation of the centerline of the section of the blood vessel, which is formed as a contiguous pixel line, can be implemented as described above by post-processing of the centerline, decomposition of the post-processed centerline into segments and an approximation of the individual segments by parametric continuous functions, which yield a C1-continuous overall curve. This is advantageous in that the centerline approximated thus has a smaller discretization error and can therefore also be advantageously used to determine geometric features of the section of the blood vessel in place of the original centerline.

Preferably, the length of the contiguous pixel line is ascertained by virtue of the sum of the arc lengths of the parametric continuous functions fitted to the plurality of segments of the centerline being ascertained. The arc length of a continuous function f(x) between a start point P1 and an end point P2 is ascertained as follows:

$$B = \int_{P1}^{P2} \sqrt{1 + f'(x)} \, dx.$$

For a number of m segments, each with a start point $P1_m$ and an end point $P2_m$, the arc length $B_{approx}$ of the overall curve, which is formed from the parametric continuous functions $b_m$ fitted to the m segments, can thus be ascertained as follows:

$$B_{approx} = \sum_{j=1}^{m} \int_{P1_m}^{P2_m} \sqrt{1 + b'_m(x)} \, dx.$$

Determining the length of the contiguous pixel line over the sum of the arc lengths of the fitted parametric continuous functions is advantageous in that the length of the contiguous pixel line can be ascertained analytically and hence with great accuracy in comparison with length approximation methods.

The centerline is formed as a contiguous pixel line in the at least one image provided. Therefore, the length of the centerline in the section of the blood vessel between a start point and an end point is preferably ascertained using a computer-implemented method for determining a length of a contiguous pixel line in an image. This is advantageous in that discretization errors during the length determination are reduced. As a result, the length of the section of the blood vessel is ascertained with the greatest possible accuracy and, at the same time, with as little outlay as possible and with as little computation time as possible.

A computer-implemented method according to the disclosure for determining a length of a contiguous pixel line in an image includes the following method steps:

post-processing of the contiguous pixel line by adapting connecting structures of the pixels along the contiguous pixel line on the basis of the pixel neighborhood thereof;

decomposing the post-processed contiguous pixel line on the basis of a criterion into a plurality of contiguous segments;

fitting a parametric continuous function to each of the plurality of segments of the post-processed contiguous pixel line in each case by adapting the function parameters such that the overall curve formed from the fitted continuous functions is C1-continuous at each point;

ascertaining the length of the contiguous pixel line as sum of the arc lengths of the parametric continuous functions which are fitted to the plurality of segments of the contiguous pixel line.

This method is advantageous in that the length of the contiguous pixel line can be determined with an accuracy that is as high as possible, outlay that is as little as possible and a computation time that is as short as possible. In particular, this method reduces the discretization error, which arises from imaging the continuous line on the image sensor. These advantages are obtained by combining the individual steps of this method with the advantages and embodiments described further above.

A method according to the disclosure for determining the length of a contiguous pixel line in an image assumes that the contiguous pixel line contains no circles or branchings.

The method for determining a length of a contiguous pixel line in an image can be used to determine the length of an object in the image. To this end, a line along which the length of the object should be measured can be determined in a preparation step. Here, the line can be a straight line, for example in measuring workpieces, a centerline like in a blood vessel, or any other line. The line forms a contiguous pixel line in the image which, when traversed, has a first and a last point of intersection with an external wall of the object. These two points of intersection form the start point and the end point, between which the length of the contiguous pixel line is ascertained on the basis of the computer-implemented method according to the invention for determining a length of a contiguous pixel line in an image.

The disclosure also extends to a computer program with program code for carrying out the above-described method steps when the computer program is loaded on a computer unit and/or executed on a computer unit.

Moreover, the disclosure extends to a system for determining at least one geometric feature of a section of an object, in particular a blood vessel in an operating region, the feature being contained in the group containing length, wall thickness, internal diameter and external diameter of the blood vessel, the system including a device for providing at least one image of the section of the blood vessel in the operating region and including a computer unit, onto which a computer program with program code for carrying out the above-described method steps for determining at least one geometric feature of a section of an object, in particular a blood vessel, is loaded.

BRIEF DESCRIPTION OF THE DRAWINGS

The invention will now be described with reference to the drawings wherein:

FIG. 5A shows a blood vessel;

FIG. 5B shows a section of the blood vessel;

FIG. 5C shows an intensity profile orthogonal to the section of the blood vessel in FIG. 5B;

FIG. 5D shows a second derivative of the intensity profile in FIG. 5C;

FIG. 7A to FIG. 7H show a post-processing method for a contiguous pixel line;

DESCRIPTION OF THE PREFERRED EMBODIMENTS OF THE INVENTION

Figure 1:
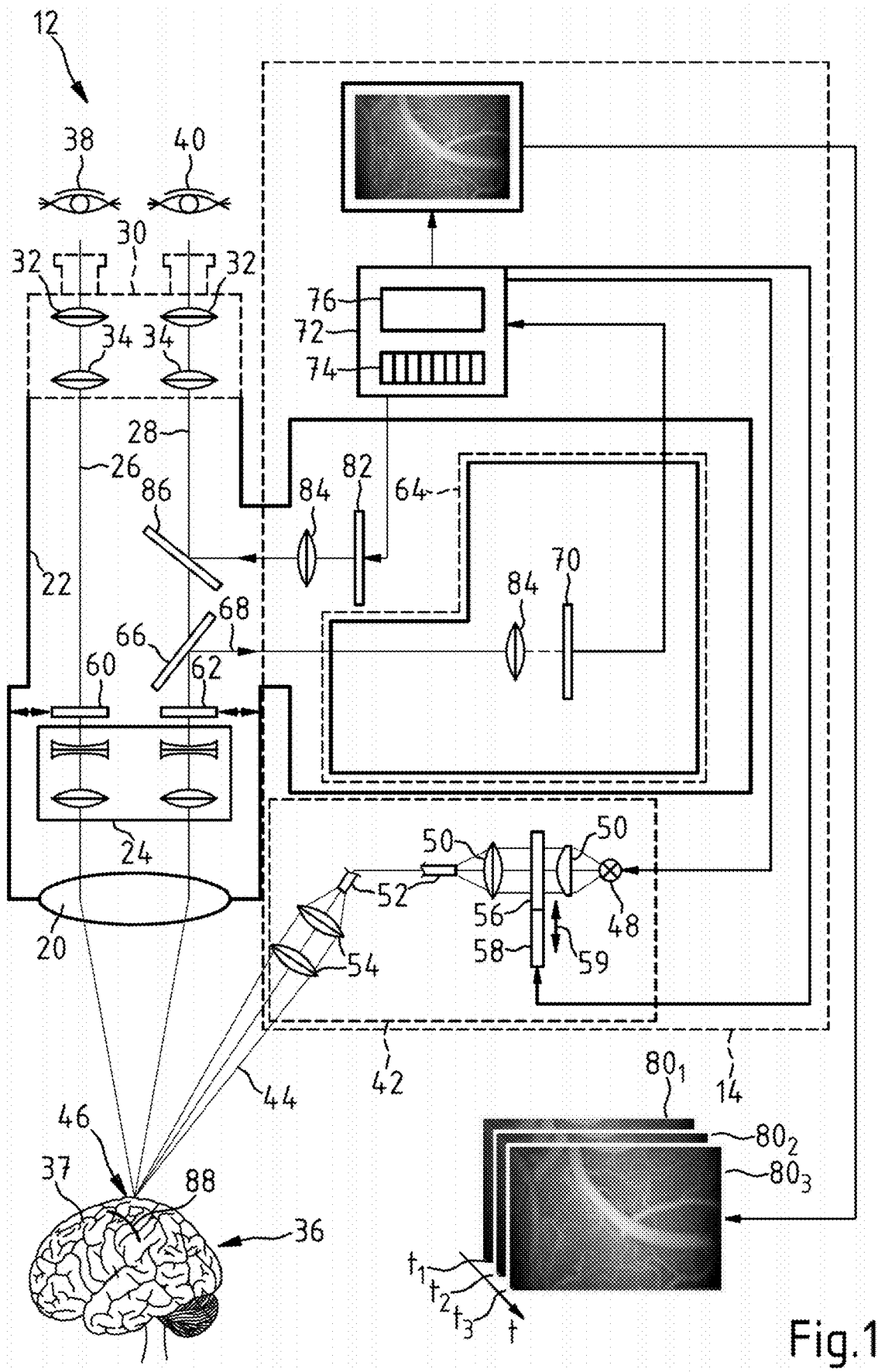
FIG. 1 shows a surgical microscope with a system for determining at least one geometric feature of a section of a blood vessel in an operating region.

The surgical microscope 12 shown in FIG. 1 contains a system 14 for determining at least one geometric feature of a section 90 of a blood vessel 88 in an operating region 36, the geometric feature being in the group including length, internal diameter and external diameter of the blood vessel, and is configured for neurosurgical operations. The surgical microscope 12 includes a microscope main objective 20. The microscope main objective 20 is received in a microscope main body 22. The microscope main body 22 contains an adjustable magnification system 24. A left and a right observation beam path 26, 28 passes through the microscope main objective 20. A binocular tube 30 is connected to a microscope main body 22. In the left and right observation beam path 26, 28, the binocular tube 30 contains an eyepiece lens 32 and a tube lens 34. By way of the binocular tube 30, an observing person is able to stereoscopically observe an operating region 36 at a brain 37 of a patient in the present case, using a left and right observer eye 38, 40.

There is an illumination device 42 in the system 14 for determining at least one geometric feature of a section 90 of a blood vessel 88 in an operating region 36. By way of an illumination beam path 44, the illumination device 42 provides illumination light 46 for the operating region 36. The illumination device 42 includes a xenon light source 48. The illumination device 42 contains further optical elements in the form of lenses 50, a light guide 52 and an illumination objective 54. The light of the xenon light source 48 is coupled into a light guide 52 via a lens system containing lenses 50. From the light guide 52, illumination light 46 reaches the operating region 36 through an illumination objective 54.

The illumination device 42 contains a switchable filter assembly for adjusting the spectral composition of the illumination light 46. This filter assembly contains an illumination filter 56. In accordance with the arrow 59, the illumination filter 56 can be moved into the illumination beam path 44 and can be moved out of the illumination beam path 44.

The illumination filter 56 is a bandpass filter. It is transmissive for light from the xenon light source 48 in the spectral range between 780 nm and 810 nm. By contrast, light in the spectral range below 780 nm and above 810 nm is filtered or significantly suppressed by the illumination filter 56.

An observation filter 60 for the left observation beam path 26 and an observation filter 62 for the right observation beam path 28 are situated in the microscope main body 22 on the side of the magnification system 24 distant from the microscope main objective 20. In accordance with the double-headed arrows, the observation filters 60, 62 can be moved into or out of the observation beam path 26, 28. Firstly, the illumination filter 56 and, secondly, the observation filters 60, 62 have a filter characteristic that is matched to one another. To observe the operating region 36 with fluorescence light, the illumination filter 56 is inserted into the illumination beam path 44 and the observation filters 60, 62 are arranged in the observation beam paths 26, 28.

The system 14 for determining at least one geometric feature of a section 90 of a blood vessel 88 in an operating region 36 in the surgical microscope 12 includes an image capturing device 64, which serves to capture images $80_1$, $80_2$, $80_3$, $80_4$, . . . of the operating region 36. Observation light from the operating region 36 can be supplied to the image capturing device 64 from the right observation beam path 28, which has an optical axis 68, through the observation filter 62 and via an output coupling beam splitter 66. There is an image sensor 70 in the image capturing device 64. The image sensor 70 is sensitive to the emission wavelength of the ICG fluorophore, which is located in the spectral range from 810 nm to 830 nm, the fluorophore being supplied to a patient for the purpose of determining at least one geometric feature of a section 90 of a blood vessel 88 in an operating region 36.

The image sensor 70 of the image capturing device 64 is connected to a computer unit 72. The computer unit 72 includes an input unit 74 and contains a program memory 76. The computer unit 72 is connected to a screen 78. Images $80_1$, $80_2$, $80_3$, $80_4$, . . . of the operating region 36 captured at different recording times $t_1$, $t_2$, $t_3$, $t_4$, . . . are displayed on the screen. The computer unit 72 controls a display 82. By way of a beam splitter 86, the display of the display 82 is overlaid on the observation light in the right observation beam path 28 via a lens 84. For an observing person, the display of the display 82 hence is visible simultaneously with the operating region 36 in the right eyepiece of the binocular tube 30.

Figure 2A:
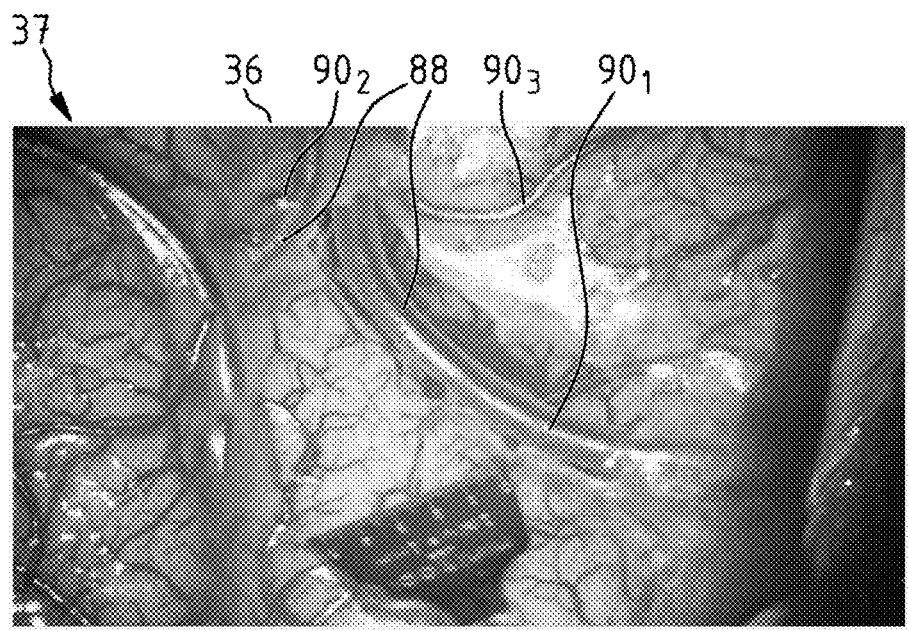
FIG. 2A shows an image of an operating region with a blood vessel.

FIG. 2A shows an operating region 36 in the brain 37 of a patient with a section $90_1$ and a section $90_2$ of a blood vessel 88.

Figure 2B:
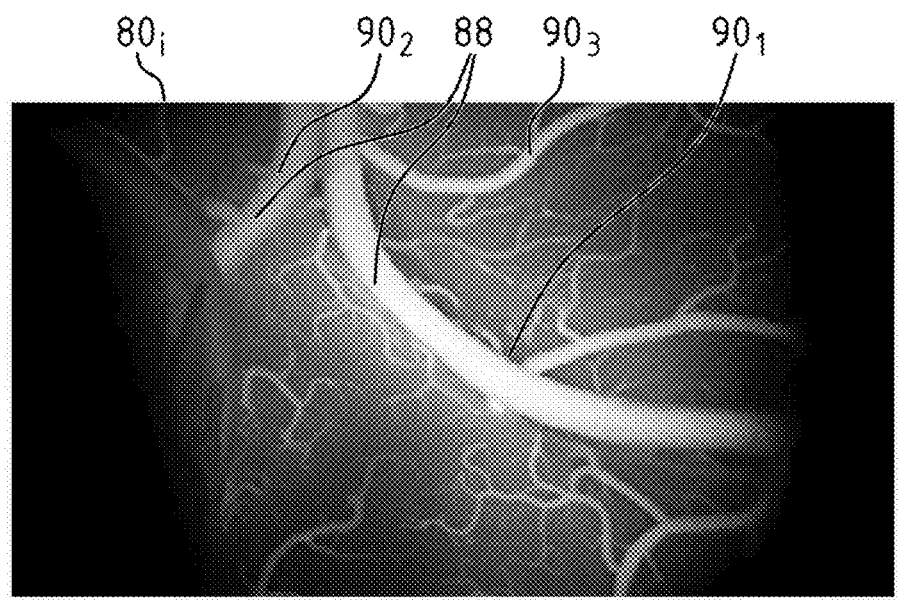
FIG. 2B shows an image of the operating region with the blood vessel of FIG. 2A, captured under fluorescence excitation light, after the addition of a fluorophore.

FIG. 2B shows an image $80_i$ of the operating region 36 in FIG. 2A, which represents a blood vessel 88 with two sections $90_1$ and $90_2$, through which blood with an added fluorophore flows, when observed with fluorescence excitation light. The observation under fluorescence light leads to the spatial extent of the blood vessel, in particular the flow channel, being better visible and hence more easily determinable.

A computer program which serves to determine at least one geometric feature of a section $90_i$ of a blood vessel 88 in an operating region 36 is loaded in the program memory 76 of the computer unit 72.

The computer program contains a blood vessel model M, which describes the geometry of a section $90_i$ of the blood vessel 88.

Figure 3:
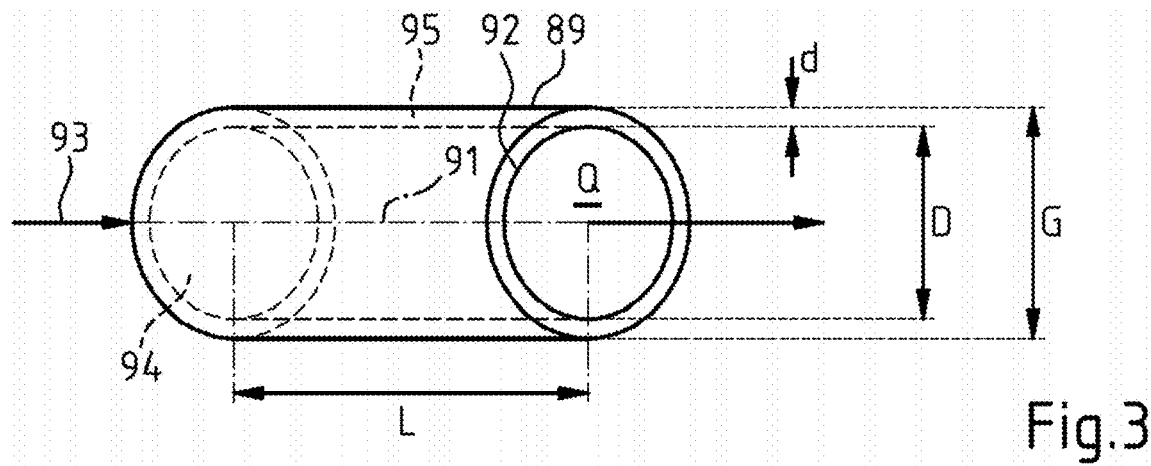
FIG. 3 shows a blood vessel model.

FIG. 3 shows a blood vessel model M, which describes a section $90_i$, i=1, 2, . . . of the blood vessel 88, shown in FIG. 2 and through which the blood of a patient flows, as a hollow cylinder of length L and with an axis of symmetry 91, the hollow cylinder having a wall 95 with a wall thickness d delimiting the latter and forming a flow channel 94, which is delimited by the side of the wall 95 of the hollow cylinder facing the axis of symmetry 91, wherein the flow channel 94 has a circular cross section Q, an internal diameter D and an external diameter G and wherein a fluid flow can pass therethrough in the direction of the arrows 93.

The parameters of the blood vessel model $M_B^Q$ are ascertained in the computer program, which is loaded into the program memory 76 of the computer unit 72, by processing at least one of the images $80_1$, $80_2$, $80_3$, $80_4$, . . . provided of the section $90_i$ of the blood vessel 88. To this end, a selected image is determined from the plurality of images $80_1$, $80_2$, $80_3$, $80_4$, . . . on the basis of a criterion in respect of the image brightness of the picture elements of the image, that is, the intensity of the picture elements. Since the fluorescence light causes a particularly high intensity of picture elements in the pictures, the state in which the blood vessel is maximally filled in the image with the fluorescence agent is determined by the following criterion:

$$I_{max} := \max\{I(x)|x \in \Omega\}$$

$$A := I_{max} \cdot |\{X \in \Omega | I(x) = I_{max}\}|.$$

where $\Omega$ denotes the set of picture elements x in an image and I(x) denotes the image brightness of the image at this picture element, referred to as the intensity of the picture element x in the present case.

Maximizing the value A ascertains the image which has a high maximum intensity $I_{max}$ and, at the same time, a large number of pixels which assume this maximum intensity value.

Figure 4A:
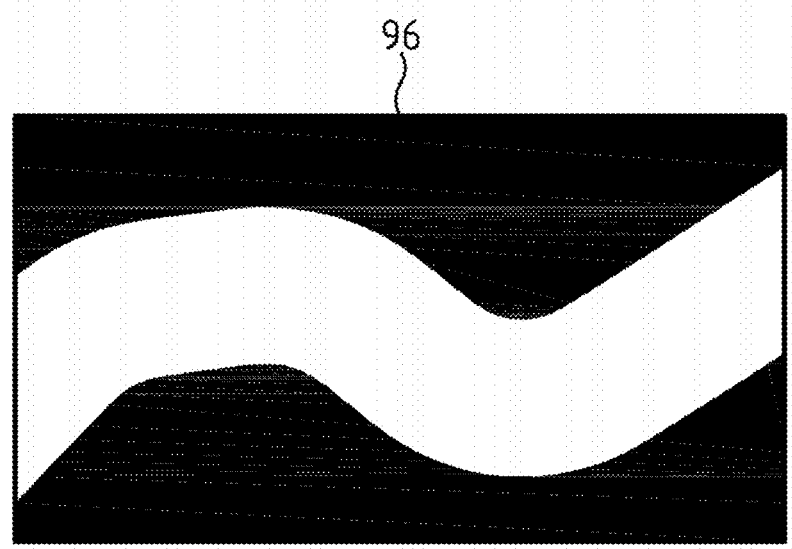
FIG. 4A shows a segmentation of a section of a blood vessel.

A segmentation 96 of the flow channel 94 of the section $90_i$ of the blood vessel 88 is then ascertained for the section $90_i$ of the blood vessel 88, as shown in FIG. 4A. This segmentation 96 is determined initially by means of Otsu thresholding, as described in the publication "Threshold Selection Method from Gray-Level Histograms," Nobuyuki Otsu, IEEE Trans. Sys. Man. Cyber. volume 9, no. 1, pp. 882-886, 1979, which is herewith referred to in its entirety and the disclosure of which is incorporated in the description of this invention. This initial segmentation 96 is post-processed by means of a gradient-based segmentation method that is explained on the basis of FIGS. 5A to 5F. The post-processed segmentation 96 corresponds to a segmentation 96 of the flow channel 94 of the section $90_i$ of the blood vessel 88. From this, it is possible to derive the relative spatial position of the side 92 of the wall 95 of the section $90_i$ of the blood vessel 88 which delimits the flow channel 94 and which faces the axis of symmetry 91.

Figure 4B:
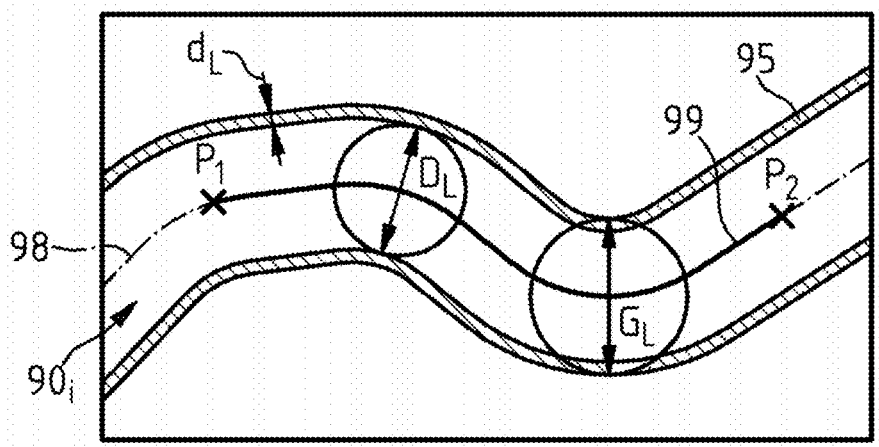
FIG. 4B shows a horizontal cross section of a blood vessel model for determining geometric features in the form of length, internal diameter and external diameter.

FIG. 4B shows a horizontal cross section of a blood vessel model M for the post-processed segmentation 96 of the section $90_i$ of the blood vessel 88 illustrated in FIG. 4A, with the parameters of the blood vessel model, which are ascertained in the computer program for determining at least one geometric feature of the section 90 of the blood vessel 88 in the operating region 36 from the segmentation 96. In this case, the centerline 98 is ascertained by means of erosion from the post-processed segmentation 96 of the section $90_i$ of the blood vessel 88. In the process, a start point $P_1$ and an end point $P_2$ of the section $90_i$ of the blood vessel 88 are defined, between which the at least one geometric feature is determined. In this case, the start point $P_1$ and the end point $P_2$ are located on the centerline 98. Moreover, the start point $P_1$ lies in a range between 5% and 15%, preferably at 10%, of the overall extent of the section $90_i$ of the blood vessel 88 along the length and the end point $P_2$ lies in a range between 80% and 95%, preferably at 90%, of the overall extent of the section $90_i$ of the blood vessel along the length. This avoids inaccuracies when determining the centerline 98, which inaccuracies occur, in particular, at the start and at the end of a section $90_i$ of a blood vessel 88.

The start point $P_1$ and the end point $P_2$ can be determined automatically by means of image processing on the basis of the centerline 98 and the specified ranges, or they can be set by a surgeon in the selected image 138.

A geometric feature in the form of the length L of the considered section $90_i$ of the blood vessel 88 is determined by virtue of ascertaining the length of the centerline section 99 of the centerline 98 between the start point $P_1$ and the end point $P_2$, as illustrated in FIGS. 7A to 7F.

To determine a further geometric feature in the form of the external diameter G of the section $90_i$ of the blood vessel 88, a local external diameter $G_L$ is ascertained at each point along the centerline 98 between the start point $P_1$ and the end point $P_2$ by virtue of a circle being defined around each point and the radius of the circle being increased until the edge of the circle touches the external wall 89 of the blood vessel 88. In this case, the external wall of the blood vessel 88 is ascertained by a segmentation 96 of the same section $90_i$ of the blood vessel 88 in an RGB image which shows the same section $90_i$ of the blood vessel 88 in the operating region 36. Then, the external diameter G of the section $90_i$ of the blood vessel 88 corresponds to the mean value of all local external diameters $G_L$.

To determine a further geometric feature in the form of the internal diameter D of the section $90_i$ of the blood vessel 88, a local internal diameter $D_L$ is ascertained at each point along the centerline 98 between the start point $P_1$ and the end point $P_2$ by virtue of a circle being defined around each point and the radius of the circle being increased until the edge of the circle touches the side 92 of the wall 95 of the blood vessel 88 facing the axis of symmetry 91. The side 92 of the wall 95 of the blood vessel 88 facing the axis of symmetry 91 can be determined in this case by ascertaining the edge of the segmentation 96 of the flow channel, as in FIGS. 5A to 5F. Then, the internal diameter D of the section $90_i$ of the blood vessel 88 corresponds to the mean value of all local internal diameters $D_L$.

To determine a further geometric feature in the form of the wall thickness d of the section $90_i$ of the blood vessel 88, the local wall thickness $d_L$ between the side 92 of the wall 95 of the blood vessel 88 facing the axis of symmetry 91 and the external wall 89 of the blood vessel is ascertained at each point along the centerline 98 between the start point $P_1$ and the end point $P_2$ by virtue of the difference between the local external diameter $G_L$ and the local internal diameter $D_L$ being ascertained at each point on the centerline 98 of the section $90_i$ of the blood vessel 88. Then, the wall thickness d of the section $90_i$ of the blood vessel 88 corresponds to the mean value of all local wall thickness values $d_L$.

Figure 5E:
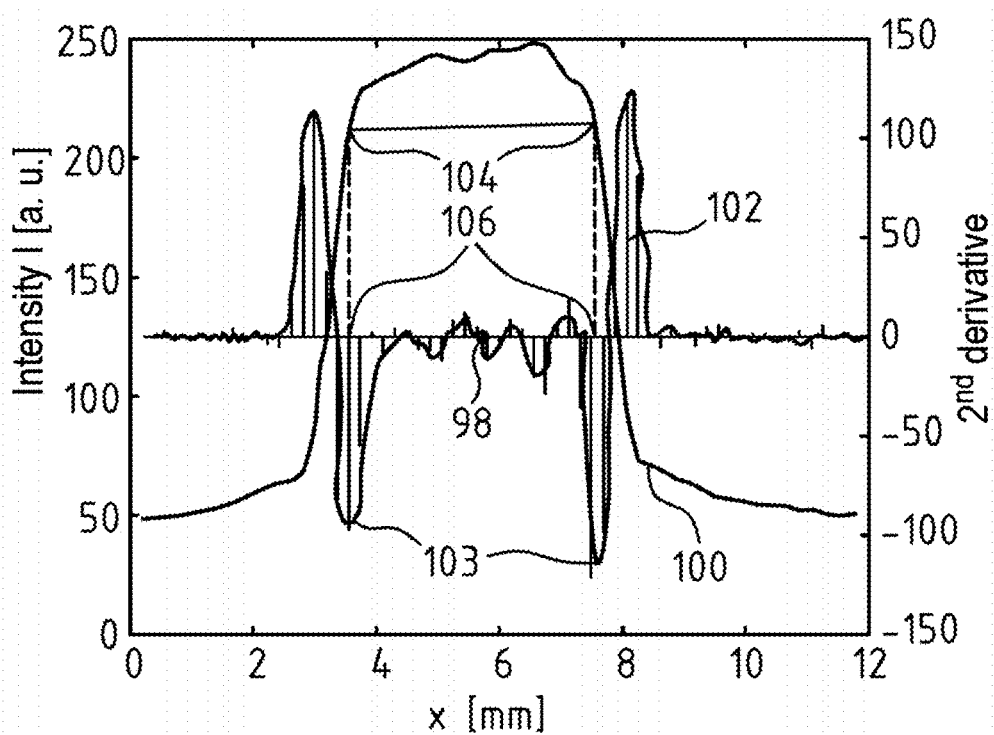
FIG. 5E shows flow channel edge points of the section of the blood vessel in FIG. 5B.

FIG. 5A to FIG. 5F explain how the relative spatial position of the side 92 of the wall 95 of the section $90_i$ of the blood vessel 88 which delimits the flow channel 94 and which faces the axis of symmetry 91 is determined in the computer program on the basis of one of the fluorescence light-based images $80_1, 80_2, 80_3, 80_4, \ldots$ captured and hence provided by means of the image capturing device 64. Since a wall 95 of the blood vessel scatters a fluorescence signal, the boundary between flow channel 94 and the wall 95 of the blood vessel is not uniquely identifiable in an image captured by means of the image capturing device 64. FIG. 5A shows a blood vessel 88 with a section $90_i$, selected therein, of one of the images $80_1, 80_2, 80_3, 80_4, \ldots$ The selected section $90_i$ of the blood vessel 88 can be seen in FIG. 5B. A local intensity profile I(x) in the selected image is illustrated in FIG. 5C as a curve 100 along the path x, which extends orthogonal to the section $90_i$ of the blood vessel 88. The side 92 of the wall 95 which delimits the flow channel 94 of the adapted blood vessel model M and which faces the axis of symmetry 91 is ascertained from this curve 100 of the intensity profile I(x) in the selected image orthogonal to the section $90_i$ of the blood vessel 88, that is, along the path x. To this end, a boundary between the flow channel 94 and the wall 95 is defined at the so-called flow channel edge points 106, at which the curvature 102 in the form of the second derivative of the intensity profile I(x) has a minimum 103 orthogonal to the section $90_i$ of the blood vessel 88. In this case, the intensity I(x) adopts the intensity value 104.

The motivation for this criterion is that the inventors used a surgical microscope 12 to record images of a material with a known wall thickness, in this case a silicone tube, filled with a blood-like medium and ICG dye and examined the intensity profile I(x) orthogonal to the edge of the silicone tube in the captured images $80_1, 80_2, 80_3, 80_4, \ldots$ This was repeated for various diameters of the silicone tube and different arrangements of same under the surgical microscope 12. In the process, the inventors determined that, in particular, the curvature of the intensity profile I(x) orthogonal to the edge of the silicone tube in the captured images $80_1, 80_2, 80_3, 80_4, \ldots$ is suitable as a criterion for determining the relative spatial position of the side 92 of the wall 95 of the section $90_i$ of the blood vessel 88 which delimits the flow channel 94 and which faces the axis of symmetry 91. As shown in FIG. 5E, the curvature 102 of the curve 100 of the intensity profile I(x) is ascertained in the form of the second derivative of the intensity profile I(x). In this procedure, the boundary between the flow channel 94 and the wall 95 corresponds to the flow channel edge points 106, at which the curvature 102 of the intensity profile I(x) reaches a minimum 103 orthogonal to the section $90_i$ of the blood vessel 88.

To determine the boundary between flow channel 94 and wall 95, the computer program therefore ascertains a segmentation of the section $90_i$ of the blood vessel 88. The edge pixels 97 of the segmentation and the gradient of the edge of the segmentation at these pixels are determined from the segmentation. An intensity profile in the at least one image provided is ascertained proceeding from the edge pixels 97 of the segmentation 96, in each case in the direction of the gradient. The flow channel edge points 106 are then determined as those points at which the curvature 102 of the intensity profile I(x) in the form of the second derivative has a minimum 103.

Figure 5F:
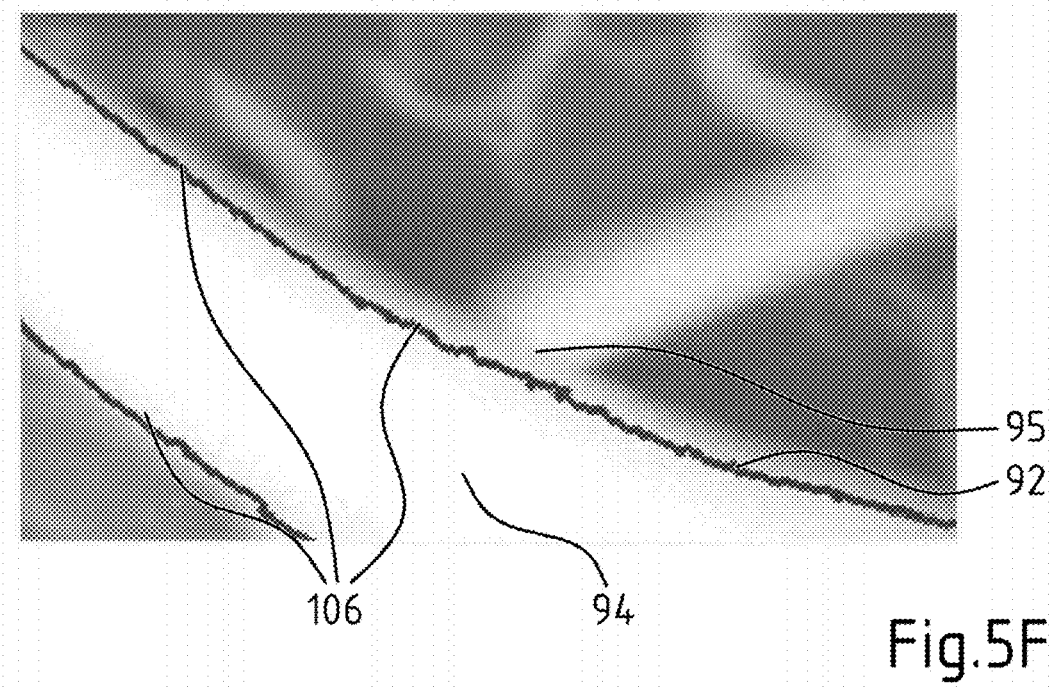
FIG. 5F shows an ascertained flow channel of the section of the blood vessel in FIG. 5B.

As illustrated in FIG. 5E, the flow channel edge points 106 define the relative spatial position of the side 92 of the wall 95 of the section $90_i$ of the blood vessel 88 which delimits the flow channel 94 and which faces the axis of symmetry 91. As shown in FIG. 5F, the relative spatial position of the side 92 of the wall 95 of the section $90_i$ of the blood vessel 88 which delimits the flow channel 94 and which faces the axis of symmetry 91 and also a segmentation 96 of the flow channel 94 are ascertained by connecting the flow channel edge points 106. Then, a centerline 98 of the section $90_i$ of the blood vessel 88 is determined from the segmentation 96 of the flow channel 94 by erosion. Different geometric features of the section $90_i$ of the blood vessel 88 can be determined on the basis of the centerline 98 and the relative spatial position of the side 92 of the wall 95 which delimits the flow channel 94 and which faces the axis of symmetry 91 and of the external wall 89 of the section $90_i$ of the blood vessel 88. To this end, a circle is determined along the centerline 98 for each pixel of the centerline 98 and the diameter of the circle is increased until the edge of the circle touches the side 92 of the wall 95 of the section $90_i$ of the blood vessel 88 which delimits the flow channel 94 and which faces the axis of symmetry 91. The local diameter of the flow channel 94 ascertained thus corresponds to the local internal diameter $D_L$ of the section $90_i$ of the blood vessel 88. The diameter of the flow channel 94, which corresponds to the internal diameter D of the section $90_i$ of the blood vessel 88, is determined by averaging the local diameters $D_L$ for all points on the centerline 98. The external diameter G of the section $90_i$ of the blood vessel 88 can be ascertained in the same way on the basis of the centerline 98 and the external wall 89. The distance between a flow channel edge point 106 and the external wall 89 of the blood vessel 88 then corresponds to the local wall thickness $d_L$. This is likewise averaged for all points along the centerline 98 and the wall thickness d of the section $90_i$ of the blood vessel 88 is determined therefrom.

Figure 6:
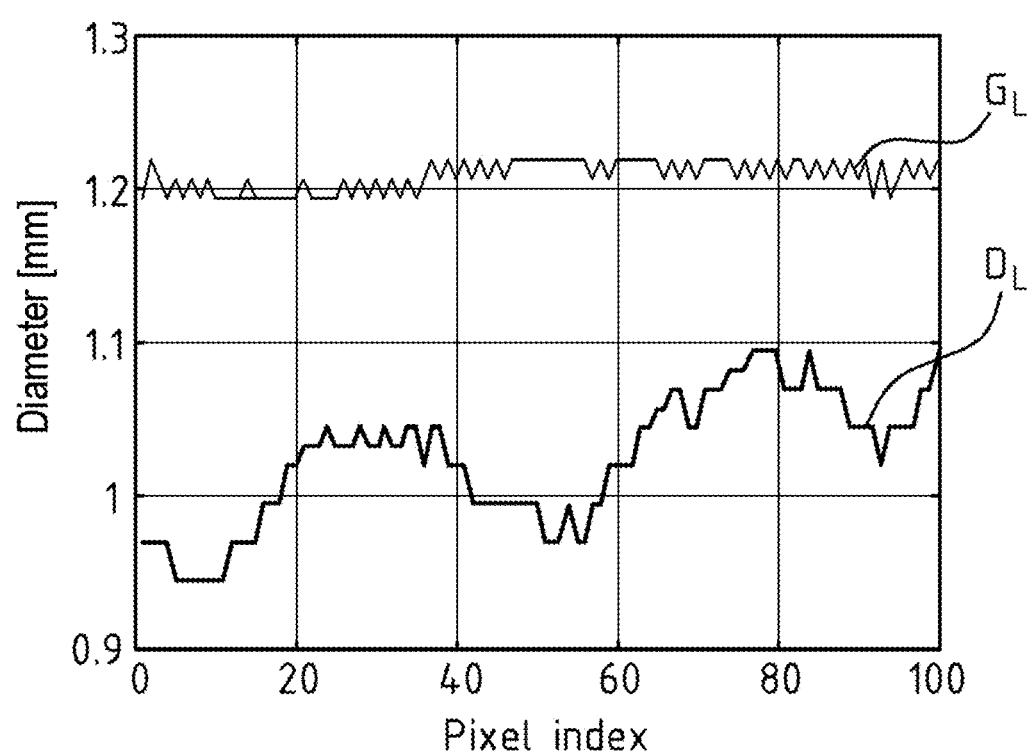
FIG. 6 shows a profile of an internal diameter and an external diameter along a centerline of a section of a blood vessel.

FIG. 6 illustrates the ascertained profile of the local external diameter $G_L$ and the ascertained profile of the local internal diameter $D_L$ for a sequence of 100 pixels along a centerline 98 of a section $90_i$ of a blood vessel 88. Information items about a known ratio of the internal diameter and the external diameter of a human blood vessel can be used when ascertaining the relative spatial position of the side 92 of the wall 95 of the section $90_i$ of the blood vessel 88 which delimits the flow channel 94 and which faces the axis of symmetry 91 in the at least one image provided. The difference between external diameter G and internal diameter D corresponds to twice the wall thickness d. As described in Nakagawa, D. et al., Wall-to-lumen ratio of intracranial arteries measured by indocyanine green angiography," Asian Journal of Neurosurgery, 2016, volume 11, no. 4, pp. 361-364, an average human arterial wall has a normally distributed so-called wall-to-lumen ratio (WLR) of $$WLR := \frac{G-D}{2D} = \frac{d}{D} = 0.086 \pm 0.022,$$

where the mean value is 0.086 and the standard deviation is 0.022. This information item can be used to determine outliers in the flow channel edge points 106 or along the external wall 89 of the section $90_i$ of the blood vessel 88 by virtue of local WLR values outside of a confidence interval in relation to a set level of significance, for example, 1%, being marked as erroneous.

Figure 17:
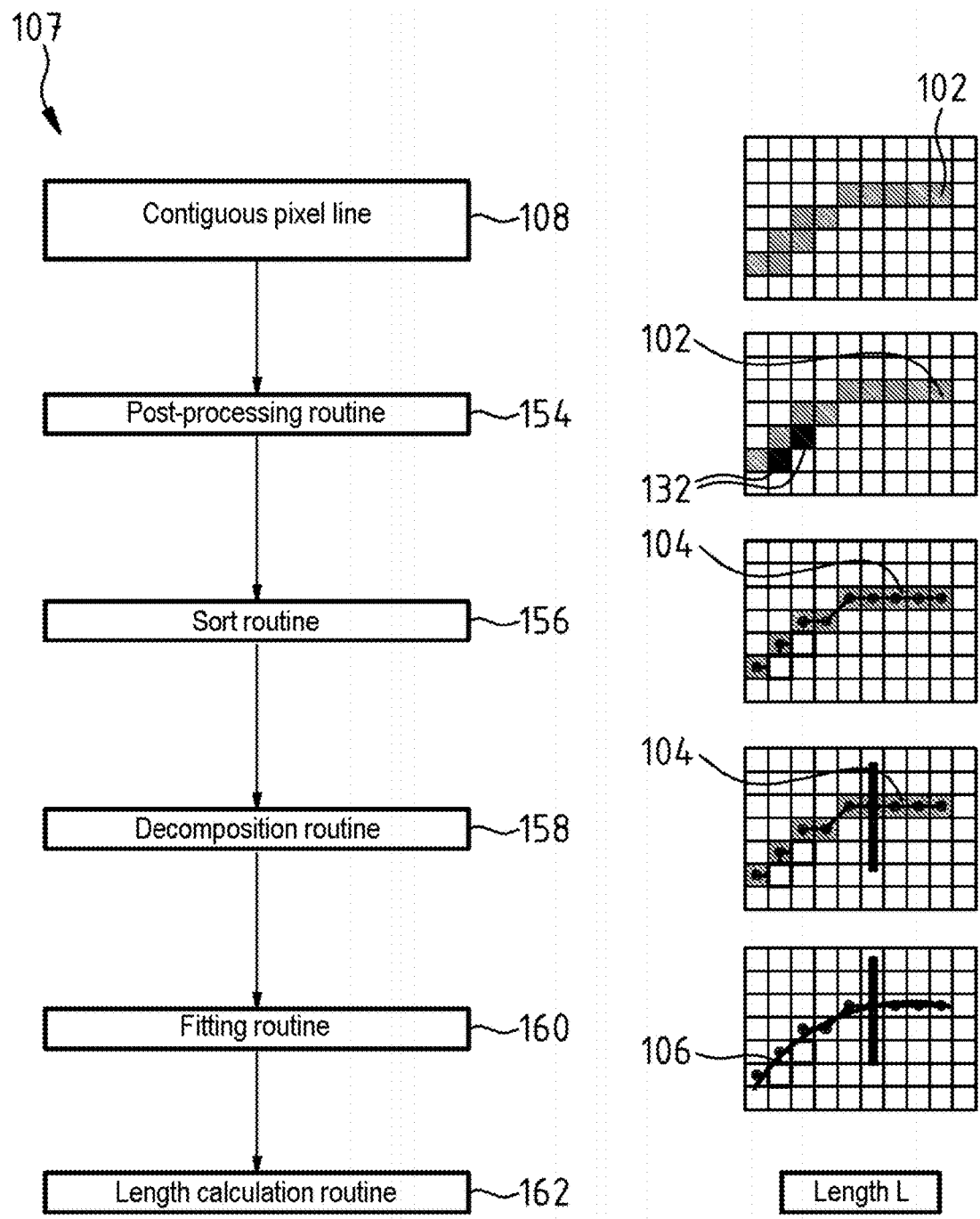
FIG. 17 shows a flowchart of a method for determining the length of an object along a contiguous pixel line in an image.

FIGS. 7A to 7H explain how a length of the centerline section 99 in the form of the centerline 98 of the considered section $90_i$ of the blood vessel 88 between the start point $P_1$ and the end point $P_2$ is determined. Here, the centerline section 99 is available as a contiguous pixel line 108, the length of which is ascertained by means of a method 107 for determining length. As illustrated in FIG. 17, the method 107 contains a post-processing routine 154, a sort routine 156, a decomposition routine 158, a fitting routine 160 and a length calculation routine 162.

FIG. 7A shows a section $90_i$ of the blood vessel 88 with the centerline 98. In the image capturing device 64, the section $90_i$ of the blood vessel 88 is imaged on a region 71 of the image sensor 70 of the image capturing device 64 shown in FIG. 7B with a resolution evident from FIG. 7C. FIG. 7D shows the discretized centerline on the image sensor 70 in the form of a contiguous pixel line 108. FIG. 7E shows a post-processed contiguous pixel line 110, in which the marked pixels are removed. To this end, the computer program contains a post-processing routine 154 which post-processes the discretized contiguous pixel line 108 in order to avoid discretization errors where possible when determining the length of the centerline 98 between the start point $P_1$ and the end point $P_2$. These discretization errors are 6.3% on average, as described in the article A. Naber, D. Berwanger, W. Nahm, "In Silico Modelling of Blood Vessel Segmentations for Estimation of Discretization Error in Spatial Measurement and its Impact on Quantitative Fluorescence Angiography," 41st Annual International Conference of the IEEE Engineering in Medicine and Biology Society (EMBC), 2019, as the result of experiments. The pixels of the post-processed contiguous pixel line 110 are sorted such that a sorted contiguous pixel line 112 in the form of a polygonal chain arises. As shown in FIG. 7G, the sorted contiguous pixel line 112 is decomposed into segments 114, 114' with segment boundaries 116. As shown in FIG. 7H, continuous functions 118, 118' in the form of Bézier curves are fitted to the individual segments 114, 114' and the length L of the centerline section 99 of the section $90_i$ of the blood vessel 88 between the start point $P_1$ and the end point $P_2$ is calculated as the sum of the arc integrals of the Bézier curves. To this end, the computer program contains a fitting routine 160 and a length calculation routine 162. This algorithm for determining length is particularly suitable for reducing the discretization error. The individual steps are explained on the basis of the following figures.

Figure 8:
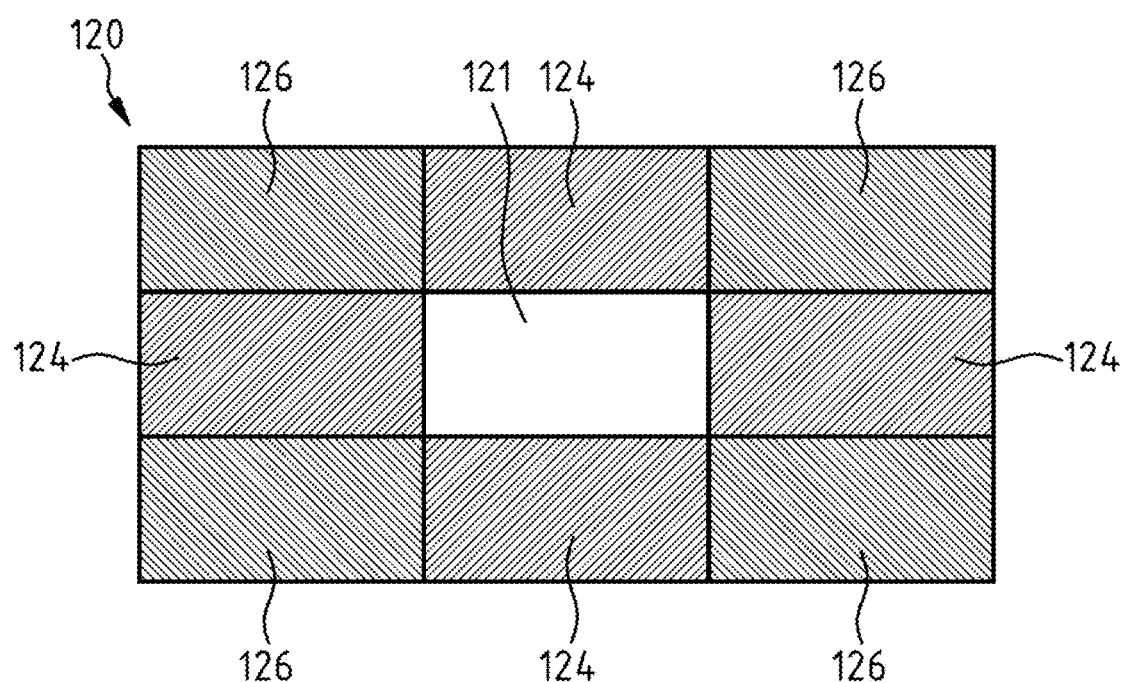
FIG. 8 shows direct and indirect neighbors of an initial pixel in an 8-connection pixel neighborhood.

FIG. 8 shows an 8-connected pixel neighborhood 120 of an initial pixel 122 with its neighboring pixels 124, 126, which are directly neighboring pixels 124 of the initial pixel 122 or indirectly neighboring pixels 126 of the initial pixel 122. Direct neighbors are characterized in that the distance in pixels from the initial pixel is exactly 1. By contrast, the distance in pixels of indirect neighbors 126 from the initial pixel is $\sqrt{2}$.

Figure 9A:
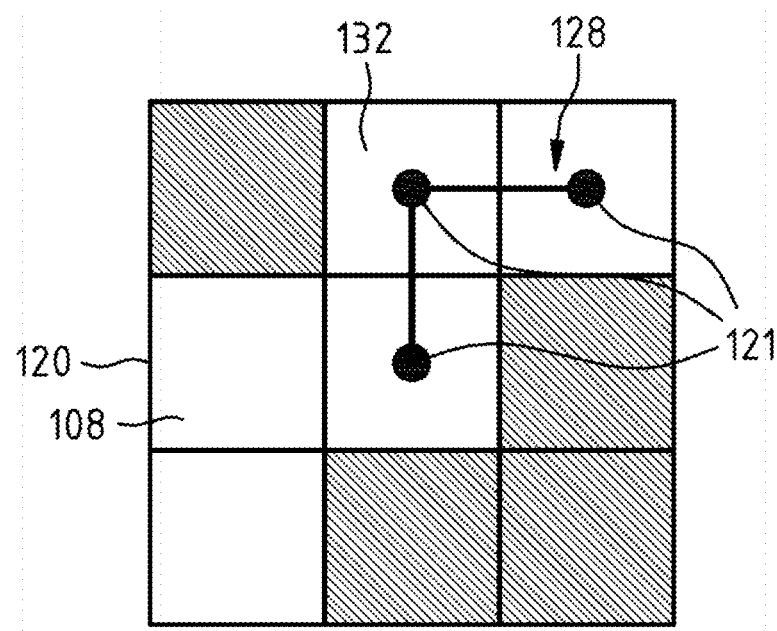
FIG. 9A shows a section of the contiguous pixel line shown in FIG. 7D.
Figure 9B:
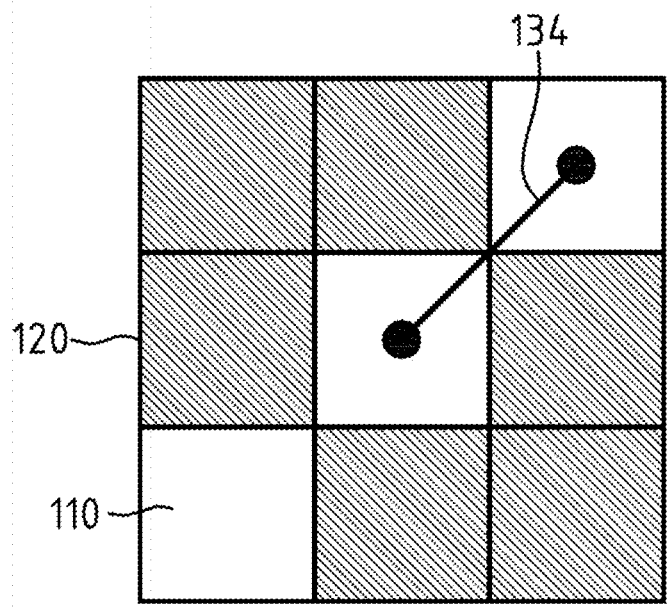
FIG. 9B shows post-processing of the section of the contiguous pixel line shown in FIG. 9A.

FIGS. 9A and 9B explain the post-processing routine 154 of the computer program, which post-processes a contiguous pixel line 108 in order to reduce discretization errors and thereby, in particular, improve the determination of length. During the post-processing, the centerline 98 is post-processed by adapting connecting structures of the pixels, that is, the pixel configurations, along the contiguous pixel line 108 on the basis of the pixel neighborhoods 120 thereof to form adapted connecting structures 134. In particular, the number of connecting structures occurring along the contiguous pixel line 108 of the centerline 98 is reduced in the process. To this end, pixels are removed from the contiguous pixel line 108. As shown in FIGS. 9A and 9B, the post-processing routine 154 of the computer program corrects the contiguous pixel line 108 of the centerline 98 by considering pixel neighborhoods 120. To this end, the pixel neighborhood 120 which surrounds each pixel along the centerline 98 and is in the form of the 8-connected pixel neighborhood is considered for each pixel along the centerline 98. L-shaped connecting structures as in FIG. 9A are replaced in the process by diagonal connecting structures in FIG. 9B. To this end, pixel groups 128 with in each case three successive pixels along the contiguous pixel line 108 are detected in a first step, wherein one pixel in each pixel group 128 is a directly neighboring pixel 124 of the other two pixels of the pixel group 128 and wherein the pixels of the pixel groups 128 define a right triangle 130. In a second step, the pixel 132 opposite the base of the right triangle 130 is removed from each pixel group 128. In this way, a post-processed contiguous pixel line 110 arises from the contiguous pixel line 108.

Figure 10:
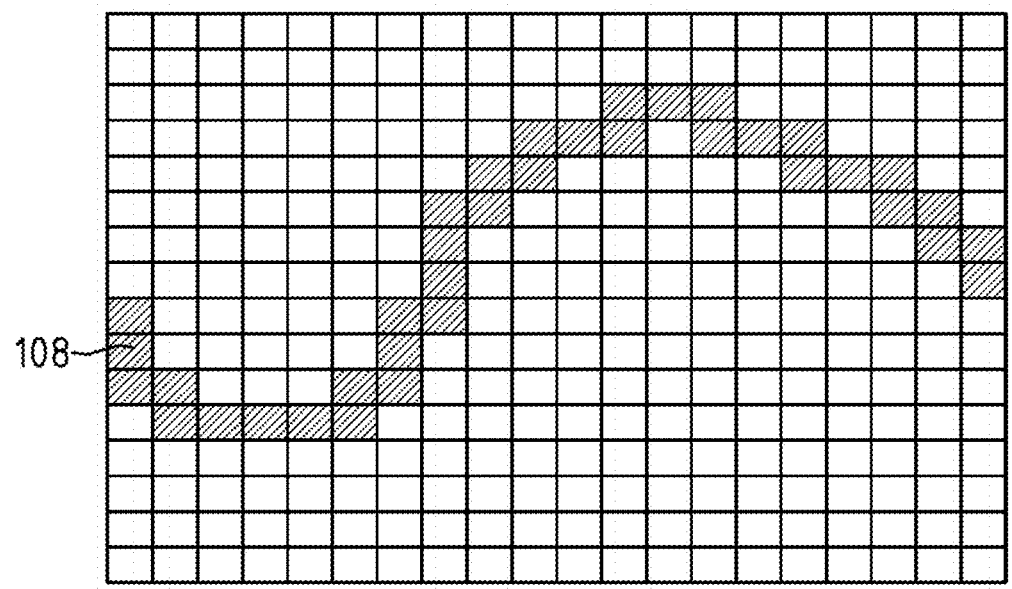
FIG. 10 shows a contiguous pixel line.
Figure 11:
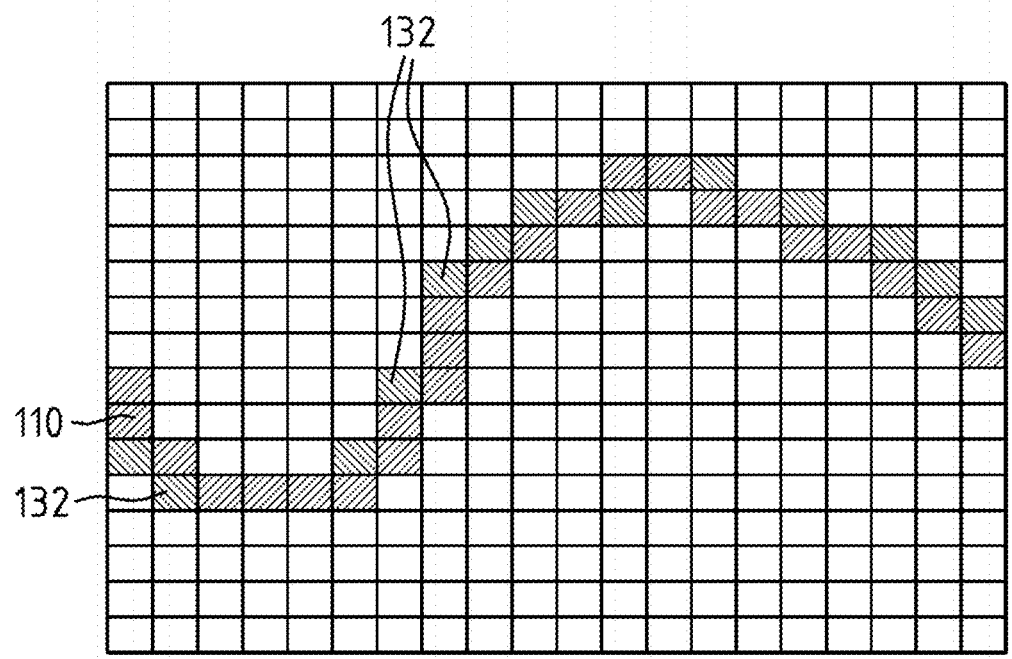
FIG. 11 shows post-processing of the contiguous pixel line of FIG. 10.

FIGS. 10 to 13 explain the steps of the method of determining length for the contiguous pixel line 108 in FIG. 10.

The post-processing routine 154 adapts the connecting structures of the pixels along the contiguous pixel line in FIG. 10, as explained in FIGS. 9A and 9B. In the process, pixel groups 128 of three pixels each are detected, wherein one pixel in each pixel group is a directly neighboring pixel of the other two pixels of the pixel group and wherein the pixels of the pixel groups 128 define a right triangle 130. The pixels 132 lying opposite the base of the right triangle 130 are removed from the contiguous pixel line 108, as a result of which a post-processed contiguous pixel line 110 arises. By reducing the number of connecting structures, it is possible to assign a unique sort to the pixels along the post-processed contiguous pixel line 110 in the sort routine 156. This is because each pixel—apart from the start and end pixel of the post-processed contiguous pixel line 110—has exactly two neighboring pixels within the pixel neighborhood 120 considered, and so a path from the start point to the end point of the post-processed contiguous pixel line 110 is uniquely determined.

Figure 12:
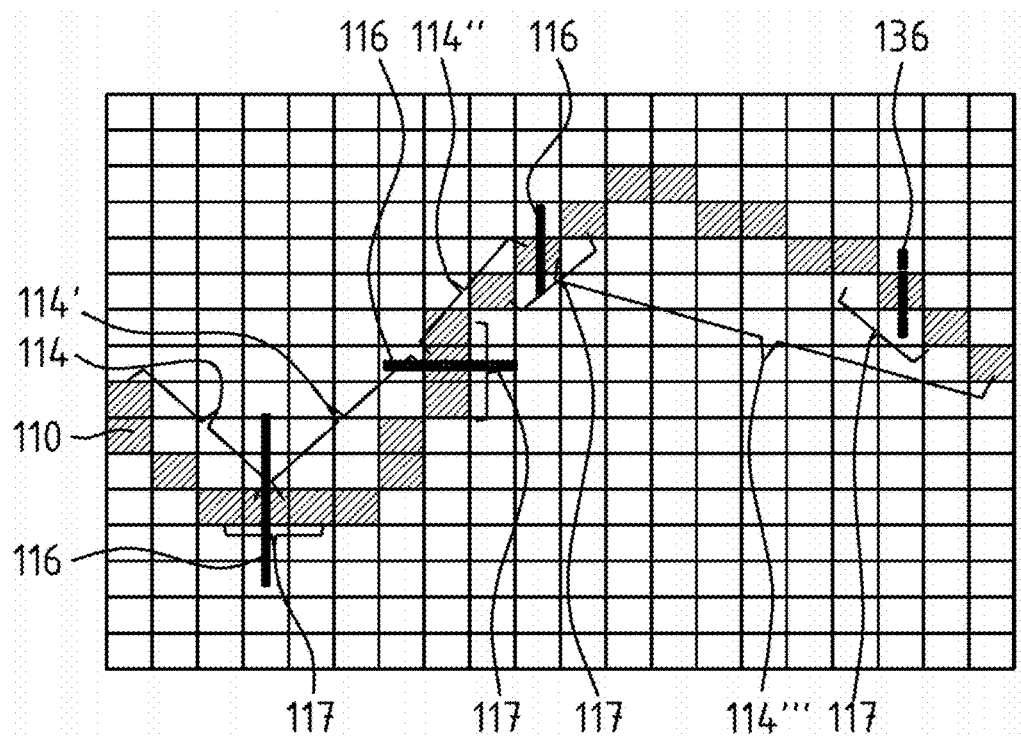
FIG. 12 shows a decomposition of the post-processed contiguous pixel line of FIG. 11 into segments.

FIG. 12 elucidates the decomposition of the post-processed contiguous pixel line 110 into segments 114, 114', 114'', 114''' in the decomposition routine 158. The following criteria are considered during the decomposition:

Each segment 114, 114', 114'', 114''' contains at least four pixels, with pixels on segment boundaries belonging to both adjacent segments.

The segment boundaries are set in such a way that the pixel of the segment boundary forms collinear pixels 117 with the preceding pixel and the subsequent pixel; that is, these lie along one line.

The post-processed contiguous pixel line 110 is traversed from its start pixel to its end pixel in the sequence set by the sort routine 156. The start pixel is the first pixel of the first segment 114. The fourth pixel of the first segment 114 is not collinear with the preceding and the subsequent pixel. Only the fifth pixel forms collinear pixels 117 with the preceding pixel and the subsequent pixel. Therefore, a segment boundary 116 is set at this pixel and the first segment 114 is terminated. The pixel of the segment boundary 116 is the first pixel of the next segment 114' at the same time. There are collinear pixels 117 at the antepenultimate pixel of the post-processed contiguous pixel line. However, no segment boundary 136 is inserted here because otherwise the last segment would contain fewer than four pixels. Therefore, the last two pixels of the post-processed contiguous pixel line 110 are added to the segment 114'''.

Figure 13:
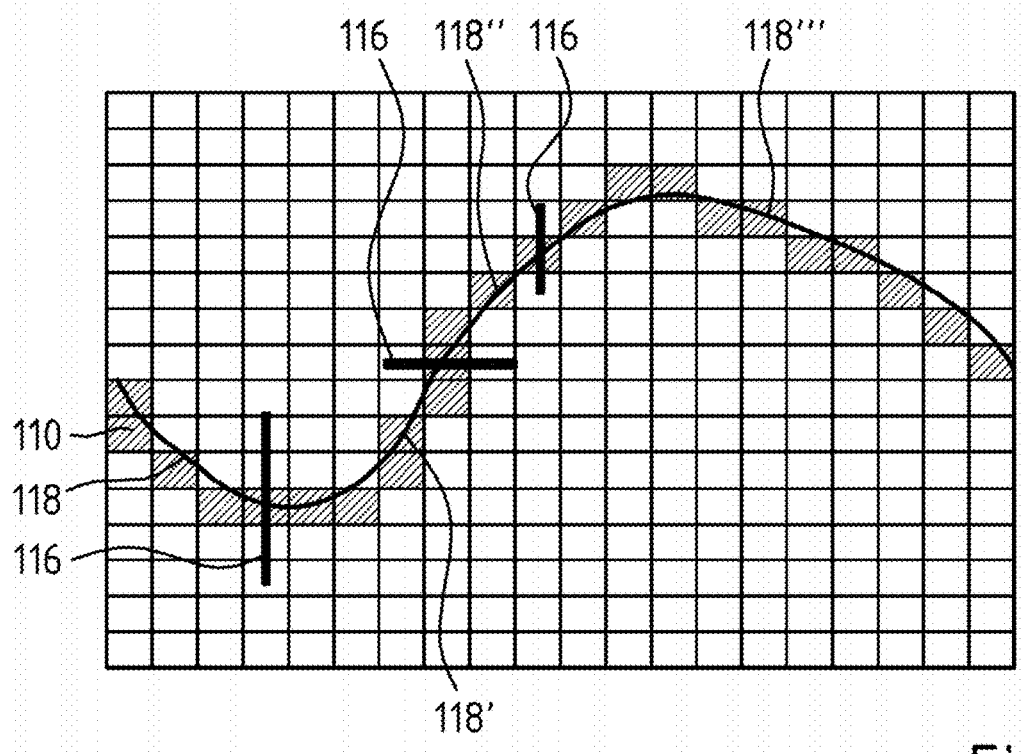
FIG. 13 shows an approximation of the segments in FIG. 12 by means of a respective Bézier curve.

As illustrated in FIG. 13, continuous functions 118, 118', 118", 118'" are fitted to the individual segments 114, 114', 114", 114'" in the fitting routine 160. Bézier curves are chosen as continuous functions. The control points of a Bézier curve in a segment 114, 114', 114", 114'" in this case correspond to the pixel centers 121 of the pixels belonging to this segment 114, 114', 114", 114'". On account of the collinearity of the pixels at the segment boundaries 116, the overall curve formed from the individual fitted continuous functions 118, 118', 118", 118'" is C1 continuous. The length of the contiguous pixel line 108 is calculated in the length calculation routine 162 by virtue of ascertaining the sum of the arc lengths of the individual continuous functions 118, 118', 118", 118'" which were fitted to the segments 114, 114', 114", 114'". In this way, a particularly simple and fast approximation of the contiguous pixel line 108 is achieved and discretization errors within the scope of the length calculation are reduced.

Figure 14:
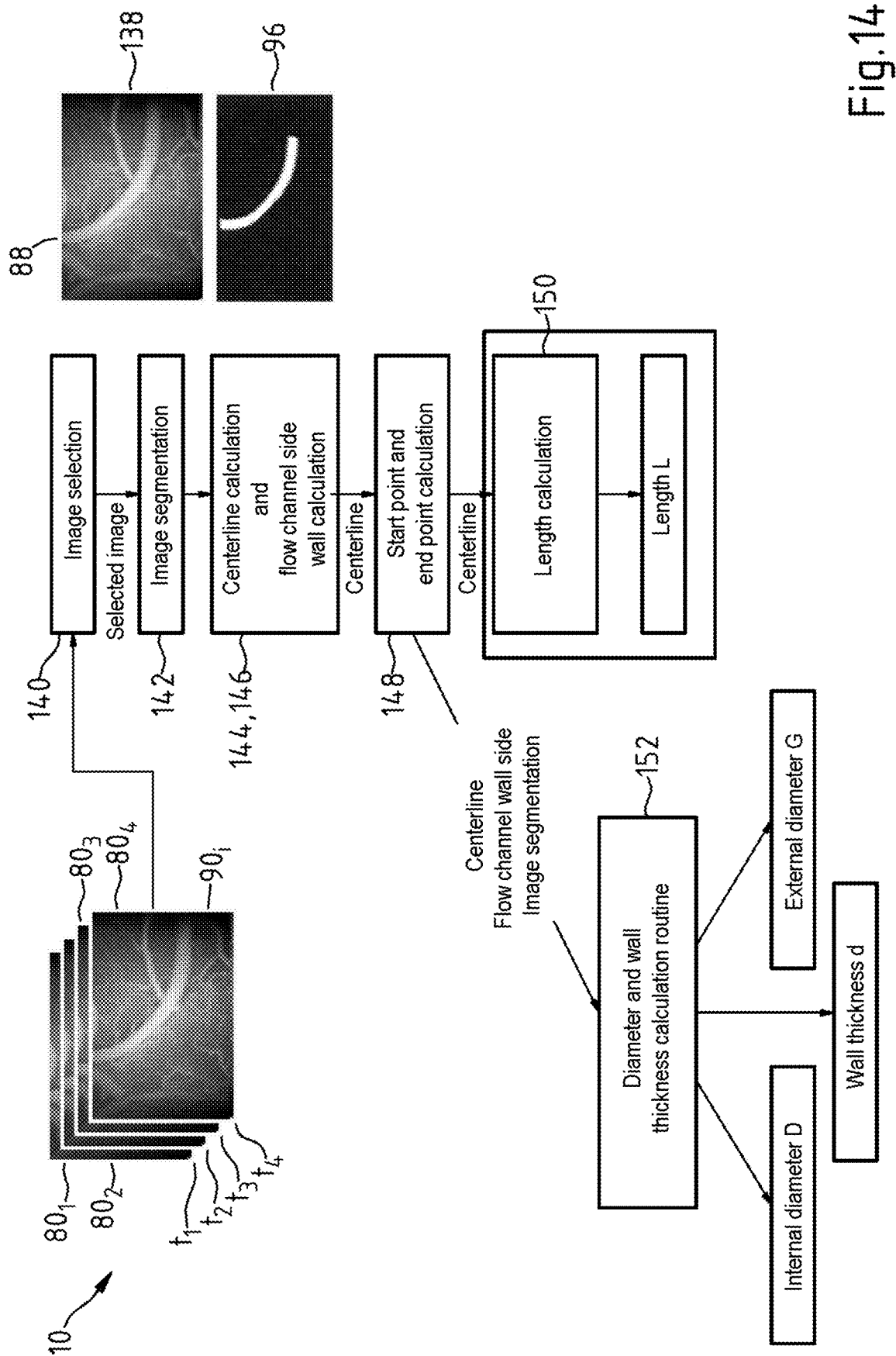
FIG. 14 shows a flowchart of a first method for determining at least one geometric feature of a section of a blood vessel in an operating region.

FIG. 14 shows a flowchart of a method 10 for determining at least one geometric feature of a section $90_i$ of a blood vessel 88 in an operating region 36. In an image selection step 140, an image is selected from the images $80_1$, $80_2$, $80_3$, $80_4$, . . . provided. The selected image 138 is segmented in an image segmentation step 142. From the segmentation 96, a centerline 98 is determined in a centerline calculation step 144 and a side 92 of the wall 95 of the blood vessel 88 which delimits the flow channel 94 and which faces the axis of symmetry 91 is determined in a flow channel wall side calculation step 146. A start point $P_1$ and an end point $P_2$ of the centerline 98 is ascertained in a start and end point calculation step 148. Then, a geometric feature of the section $90_i$ of the blood vessel 88 in the form of the length of the section $90_i$ of the blood vessel 88 is determined by ascertaining the length of the centerline section 99 between the start point $P_1$ and the end point $P_2$ in a length calculation step 150. By way of example, the number of pixels in the centerline section 99 can serve as the length of the centerline section 99.

As an alternative or in addition to the length, one or more further geometric features of the section $90_i$ of the blood vessel 88 in the form of the internal diameter D, the external diameter G and/or the wall thickness d are ascertained, as described above on the basis of FIGS. 4 to 6, from the centerline 98, the segmentation 96 of the section $90_i$ of the blood vessel 88 and the side 92 of the wall 95 of the blood vessel 88 which delimits the flow channel 94 and which faces the axis of symmetry 91.

Figure 15:
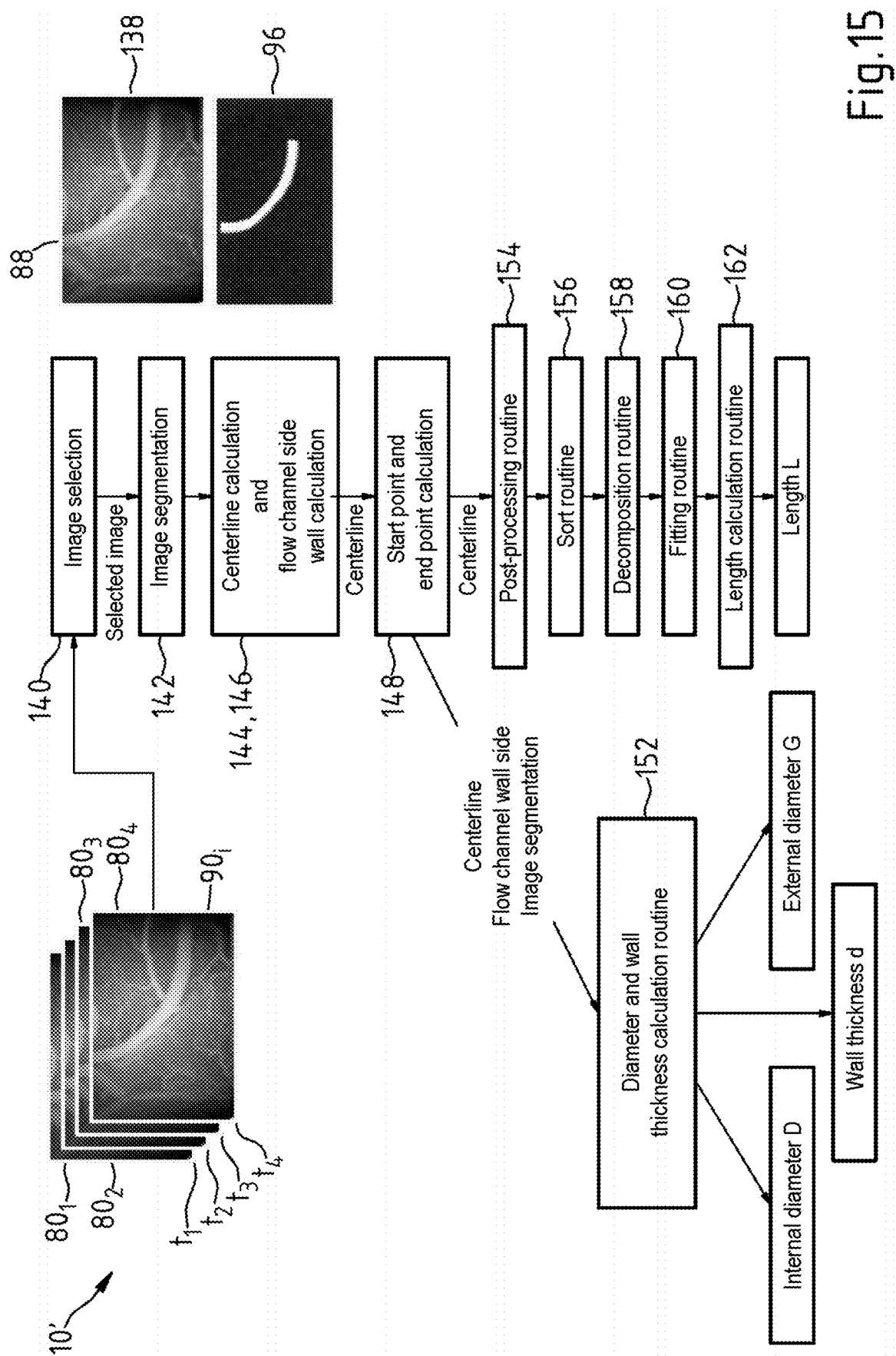
FIG. 15 shows a flowchart of a second method for determining at least one geometric feature of a section of a blood vessel in an operating region.

FIG. 15 shows a flowchart of a further method 10' for determining at least one geometric feature of a section $90_i$ of a blood vessel 88 in an operating region 36. In an image selection step 140, an image is selected from the images $80_1$, $80_2$, $80_3$, $80_4$, . . . provided. The selected image 138 is segmented in an image segmentation step 142. From the segmentation 96, a centerline 98 is determined in a centerline calculation step 144 and a side 92 of the wall 95 of the blood vessel 88 which delimits the flow channel 94 and which faces the axis of symmetry 91 is determined in a flow channel wall side calculation step 146. A start point $P_1$ and an end point $P_2$ of the centerline 98 are ascertained in a start and end point calculation step 148. The centerline section 99 corresponds to a contiguous pixel line 108. The centerline 98 is post-processed in a post-processing routine 154, as described on the basis of FIG. 9, and the pixels are sorted in a sort routine 156. The post-processed centerline is decomposed into segments 114 in a decomposition routine 158 and continuous functions 118 are fitted to the segments in a fitting routine 160. Then, a geometric feature of the section $90_i$ of the blood vessel 88 in the form of the length of the section $90_i$ of the blood vessel 88 is determined by ascertaining the sum of the arc lengths of the fitted continuous functions 118 in a length calculation routine 162.

As an alternative or in addition to the length, one or more further geometric features of the section $90_i$ of the blood vessel 88 in the form of the internal diameter D, the external diameter G and/or the wall thickness d are ascertained, as described above on the basis of FIGS. 4 to 6, from the centerline 98, the segmentation 96 of the section $90_i$ of the blood vessel 88 and the side 92 of the wall 95 of the blood vessel 88 which delimits the flow channel 94 and which faces the axis of symmetry 91.

Figure 16:
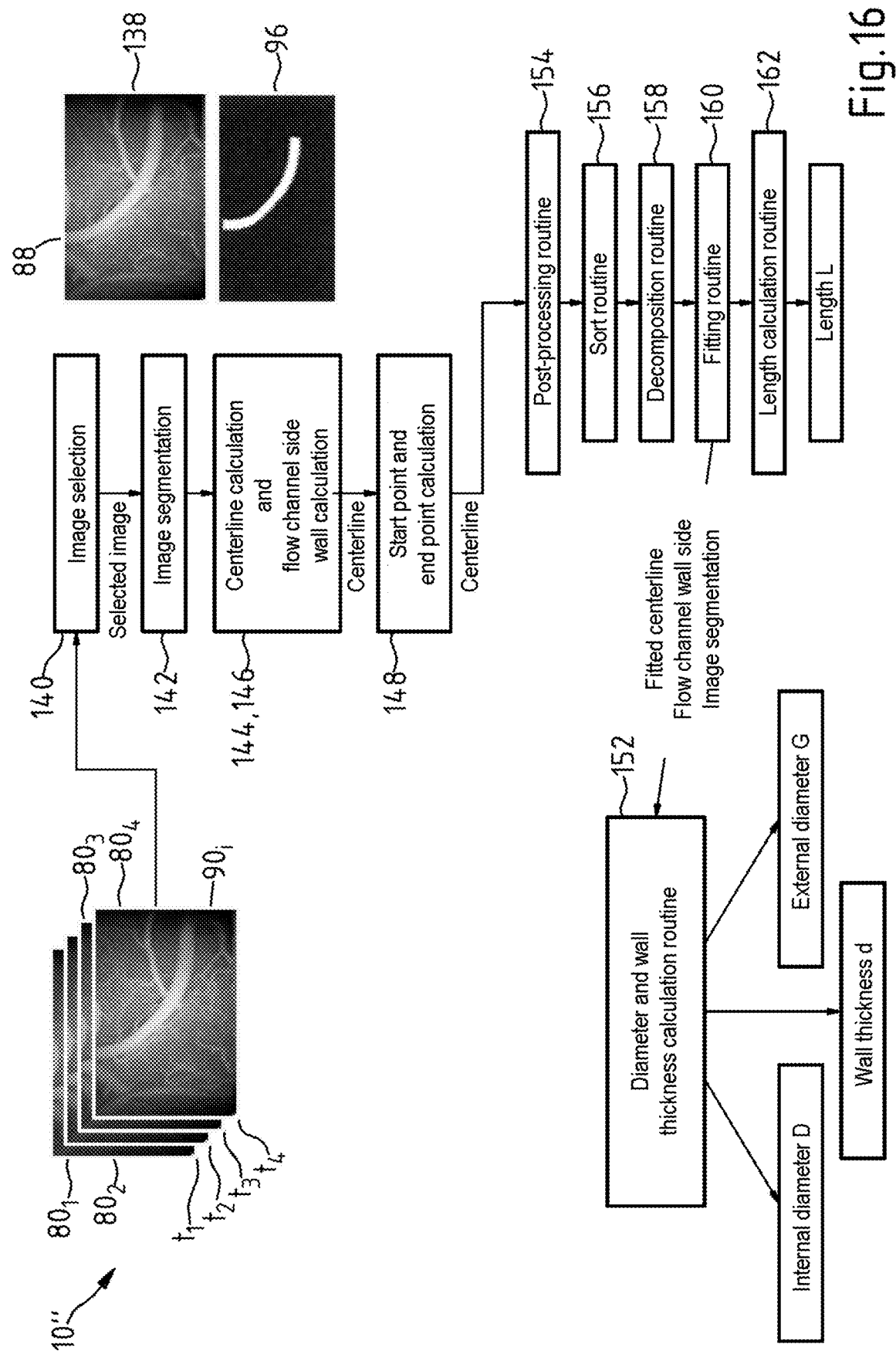
FIG. 16 shows a flowchart of a third method for determining at least one geometric feature of a section of a blood vessel in an operating region.

FIG. 16 shows a flowchart of a further method 10" for determining at least one geometric feature of a section $90_i$ of a blood vessel 88 in an operating region 36. In an image selection step 140, an image is selected from the images $80_1$, $80_2$, $80_3$, $80_4$, . . . provided. The selected image 138 is segmented in an image segmentation step 142. From the segmentation 96, a centerline 98 is determined in a centerline calculation step 144 and a side 92 of the wall 95 of the blood vessel 88 which delimits the flow channel 94 and which faces the axis of symmetry 91 is determined in a flow channel wall side calculation step 146. A start point $P_1$ and an end point $P_2$ of the centerline 98 are ascertained in a start and end point calculation step 148. The centerline section 99 corresponds to a contiguous pixel line 108. The centerline 98 is post-processed in a post-processing routine 154, as described on the basis of FIG. 9, and the pixels are sorted in a sort routine 156. The post-processed centerline is decomposed into segments 114 in a decomposition routine 158 and continuous functions 118 are fitted to the segments in a fitting routine 160. Then, a geometric feature of the section $90_i$ of the blood vessel 88 in the form of the length of the section $90_i$ of the blood vessel 88 is determined by ascertaining the sum of the arc lengths of the fitted continuous functions 118 in a length calculation routine 162.

As an alternative or in addition to the length, one or more further geometric features of the section $90_i$ of the blood vessel 88 in the form of the internal diameter D, the external diameter G and/or the wall thickness d are ascertained, as described above on the basis of FIGS. 4 to 6, from the fitted centerline in the form of the overall curve of the continuous functions 118 which were fitted to the segments 114 of the post-processed centerline, the segmentation 96 of the section $90_i$ of the blood vessel 88 and the side 92 of the wall 95 of the blood vessel 88 which delimits the flow channel 94 and which faces the axis of symmetry 91.

FIG. 17 shows a flowchart of a method 107 for determining the length of an object captured by means of an image capturing device, which ascertains a length L for a contiguous pixel line 108. A post-processed contiguous pixel line 110 is determined from the contiguous pixel line 108 in a post-processing routine 154. The pixels of the contiguous pixel line 110 are sorted in a sort routine 156. The post-processed contiguous pixel line 110 is decomposed into segments 114 in a decomposition routine 158. Continuous functions 118 are fitted to the individual segments 114 in a fitting routine 160. The length L of the contiguous pixel line 108 is ascertained in a length calculation routine 162 by virtue of the arc length of the overall curve formed from the segments 114 being calculated.

In summary, the following, in particular, should be noted: The invention relates to a computer-implemented method 10, 10', 10" for determining at least one geometric feature of a section $90_1$, $90_2$, $90_3$, . . . of a blood vessel 88 in an operating region 36, the feature being contained in the group containing length L, wall thickness d, internal diameter D and external diameter G of the section $90_1$, $90_2$, $90_3$, ... of the blood vessel 88, in which at least one image $80_1$, $80_2$, $80_3$, $80_4$, ... of the section $90_1$, $90_2$, $90_3$, ... of the blood vessel 88 in the operating region 36 is provided and in which an adapted blood vessel model M is provided by means of image processing for the section $90_1$, $90_2$, $90_3$, ... of the blood vessel 88 by adapting a blood vessel model M, which describes the section $90_1$, $90_2$, $90_3$, ... of the blood vessel 88 as a flow channel 94 with a wall 95 delimiting the latter and with an axis of symmetry 91, at at least one of the images $80_1$, $80_2$, $80_3$, $80_4$, ... provided, wherein a centerline 98 of the section $90_1$, $90_2$, $90_3$ ..., of the blood vessel 88 is determined in the form of a contiguous pixel line 108 in the at least one image $80_1$, $80_2$, $80_3$, $80_4$ ..., provided, wherein a relative spatial position of the side 92 of the wall 95 which delimits the flow channel 94 and which faces the axis of symmetry 91 is ascertained on the basis of the centerline 98 and the at least one image $80_1$, $80_2$, $80_3$, $80_4$, ... provided, and wherein the at least one geometric feature of the section $90_1$, $90_2$, $90_3$, ... of the blood vessel 88 in the operating region 36 is derived from the adapted blood vessel model M. The invention also relates to a computer-implemented method for determining the length of a contiguous pixel line in an image and a system for determining at least one geometric feature of a section $90_1$, $90_2$, $90_3$, ... of an object.

It is understood that the foregoing description is that of the preferred embodiments of the invention and that various changes and modifications may be made thereto without departing from the spirit and scope of the invention as defined in the appended claims.

LIST OF REFERENCE SIGNS 10, 10', 10" Method
12 Surgical microscope
14 System for determining the blood volume flow
20 Microscope main objective
22 Microscope main body
24 Magnification system
26 Left observation beam path
28 Right observation beam path
30 Binocular tube
32 Eyepiece lens
34 Tube lens
36 Operating region
37 Brain
38 Left observer eye
40 Right observer eye
42 Illumination device
44 Illumination beam path
46 Illumination light
48 Xenon light source
50 Lens
52 Light guide
54 Illumination objective
56 First illumination filter
58 Second illumination filter
59 Arrow
60 Observation filter for the left observation beam path
62 Observation filter for the right observation beam path
64 Image capturing device
66 Output coupling beam splitter
68 Optical axis
70 Image sensor
71 Region
72 Computer unit
74 Input unit
76 Program memory
78 Screen
$80_1$ Image 1
$80_2$ Image 2
$80_3$ Image 3
$80_4$ Image 4
82 Display
84 Lens
86 Beam splitter
88 Blood vessel
89 External wall
$90_1$, $90_2$, $90_3$ Section
91 Axis of symmetry
92 Side of the wall of the blood vessel facing the axis of symmetry
93 Arrow
94 Flow channel
95 Wall
96 Segmentation
97 Edge pixel
98 Centerline
99 Centerline section
100 Curve
102 Curvature
103 Minimum
104 Point with minimum curvature
106 Flow channel edge point
107 Method
108 Contiguous pixel line
110 Post-processed contiguous pixel line
112 Sorted contiguous pixel line
114, 114', 114", 114''' Segments
116 Segment boundary
117 Collinear pixels
118, 118', 118", 118''' Continuous function
120 Pixel neighborhood
121 Pixel center
122 Initial pixel
124 Directly neighboring pixel
126 Indirectly neighboring pixel
128 Pixel group
130 Right triangle
132 Pixel opposite to the base of the right triangle
134 Adapted connecting structure
136 No segment boundary
138 Selected image
140 Image selection
142 Image segmentation
144 Centerline calculation
146 Flow channel wall side calculation
148 Start point and end point calculation
150 Length Calculation
152 Diameter and wall thickness calculation routine
154 Post-processing routine
156 Sort routine
158 Decomposition routine
160 Fitting routine
162 Length calculation routine
M Blood vessel model
$t_1$, $t_2$, $t_3$, $t_4$ Recording times
L Length of the section of the blood vessel
Q Cross section of the flow channel
D Internal diameter
$D_L$ Local diameter
G External diameter $G_L$ Local external diameter
d Wall thickness
$d_L$ Local wall thickness
$P_1, P_{1m}$ Start point
$P_2, P_{2m}$ End point
$B, B_{approx}$ Arc length

What is claimed is:

1. A computer-implemented method for determining at least one geometric feature of a section of a blood vessel in an operating region, the at least one feature being at least one of length, wall thickness, internal diameter and external diameter of the section of the blood vessel, the method comprising:
   providing at least one image of the section of the blood vessel in the operating region;
   determining an adapted blood vessel model for the section of the blood vessel by adapting a blood vessel model, which describes the section of the blood vessel as a flow channel with a wall delimiting the flow channel and with an axis of symmetry, via image processing using at least one of the images provided;
   ascertaining a relative spatial position of a side of the wall of the section of the blood vessel which delimits the flow channel and which faces the axis of symmetry in the at least one image provided;
   determining a centerline of the section of the blood vessel in a form of a contiguous pixel line in the at least one image provided from the relative spatial position of the side of the wall of the section of the blood vessel which delimits the flow channel and which faces the axis of symmetry;
   deriving the at least one geometric feature of the section of the blood vessel in the operating region from the adapted blood vessel model;
   post-processing the centerline by adapting connecting structures of pixels along the contiguous pixel line on a basis of pixel neighborhoods thereof;
   decomposing the post-processed centerline into a plurality of contiguous segments on a basis of a criterion; and,
   fitting a corresponding parametric continuous function to each of the plurality of segments of the post-processed centerline by adapting function parameters such that an overall curve formed from the fitted parametric continuous functions is C1-continuous at each point.

2. The computer-implemented method of claim 1, wherein the at least one image provided is based on fluorescence light in a form of light with wavelengths lying within a fluorescence spectrum of a fluorophore flowing through the section of the blood vessel.

3. The computer-implemented method of claim 1, wherein the blood vessel model is a hollow cylinder with the axis of symmetry and the wall has a wall thickness.

4. The computer-implemented method of claim 1, wherein the relative spatial position of the side of at least one of the wall, which delimits the flow channel and which faces the axis of symmetry, and an external wall of the blood vessel is ascertained on the basis of a segmentation of the section of the blood vessel in the at least one image provided.

5. The computer-implemented method of claim 1, wherein the at least one geometric feature is at least one of:
   the internal diameter of the blood vessel, which is ascertained as a mean value of local internal diameters of the flow channel along the centerline in the at least one image provided;
   the external diameter of the blood vessel, which is ascertained as a mean value of local external diameters along the centerline in the at least one image provided; and,
   the wall thickness of the blood vessel, which is ascertained as a mean value of local wall thickness values of the blood vessel along the centerline in the at least one image provided.

6. The computer-implemented method of claim 1, wherein information items about a known ratio of the internal diameter and the external diameter of a human blood vessel are used when ascertaining the relative spatial position of the side of the wall which delimits the flow channel and which faces at least one of the axis of symmetry and the external wall of the blood vessel in the at least one image provided.

7. The computer-implemented method of claim 1, wherein the side of the wall which delimits the flow channel of the adapted blood vessel model and which faces the axis of symmetry is ascertained on the basis of a criterion in relation to a curve of an intensity profile orthogonal to the section of the blood vessel in the at least one image provided.

8. The computer-implemented method of claim 7, wherein the criterion in relation to the curve of the intensity profile takes account of the curvature of the curve of the intensity profile orthogonal to the section of the blood vessel in the at least one image provided.

9. The computer-implemented method of claim 1, wherein a sum of arc lengths of the parametric continuous functions which are fitted to the plurality of segments of the centerline is ascertained for ascertaining the length of the section of the blood vessel.

10. The computer-implemented method of claim 1, wherein the adapting of connecting structures of the pixels along the contiguous pixel line on the basis of the pixel neighborhood thereof includes the following steps:
    detecting pixel groups, each with three successive pixels, along the contiguous pixel line, wherein one pixel in each of the pixel groups is a directly neighboring pixel of the other two pixels of the pixel group and wherein the pixels of the pixel groups define a right triangle;
    removing the pixel lying opposite the base of the right triangle from each pixel group.

11. The computer-implemented method of claim 1, wherein a collinearity of three successive pixels of the contiguous pixel line is taken into account as a criterion for decomposing the contiguous pixel line.

12. The computer-implemented method of claim 1, wherein the parametric continuous functions are formed as Bézier curves.

13. The computer-implemented method of claim 12, wherein control points of the Bézier curves in each of the plurality of segments of the contiguous pixel line correspond to pixel centers of the pixels of the contiguous pixel line in the corresponding segment.

14. A computer-implemented method for determining a length of a contiguous pixel line in an image, the method comprising:
   post-processing the contiguous pixel line by adapting connecting structures of pixels along the contiguous pixel line on a basis of a pixel neighborhood thereof;
   decomposing the post-processed contiguous pixel line into a plurality of contiguous segments on the basis of a criterion;
   fitting a corresponding parametric continuous function to each of the plurality of segments of the contiguous post-processed pixel line by adapting function parameters such that an overall curve formed from the fitted parametric continuous functions is C1-continuous at each point; and, ascertaining the length of the contiguous pixel line as a sum of arc lengths of the parametric continuous functions which are fitted to the plurality of segments of the contiguous pixel line.

15. The computer-implemented method of claim 14, wherein the adapting of connecting structures of the pixels along the contiguous pixel line on the basis of the pixel neighborhood thereof includes the following steps:

detecting pixel groups, each with three successive pixels, along the contiguous pixel line, wherein one pixel in each of the pixel groups is a directly neighboring pixel of the other two pixels of the pixel group and wherein the pixels of the pixel groups define a right triangle;

removing the pixel lying opposite the base of the right triangle from each pixel group.

16. The computer-implemented method of claim 15, wherein a collinearity of three successive pixels of the contiguous pixel line is taken into account as a criterion for decomposing the contiguous pixel line.

17. The computer-implemented method of claim 14, wherein the parametric continuous functions are formed as Bézier curves.

18. The computer-implemented method of claim 17, wherein the control points of the Bézier curves in each of the plurality of segments of the contiguous pixel line correspond to pixel centers of the pixels of the contiguous pixel line in this segment.

19. A computer program having program code stored on a non-transitory computer readable medium, said program code being configured, when executed by a processor, to:

provide at least one image of a section of a blood vessel in an operating region;

determine an adapted blood vessel model for the section of the blood vessel by adapting a blood vessel model, which describes the section of the blood vessel as a flow channel with a wall delimiting the flow channel and with an axis of symmetry, via image processing using at least one of the images provided;

ascertain a relative spatial position of a side of the wall of the section of the blood vessel which delimits the flow channel and which faces the axis of symmetry in the at least one image provided;

determine a centerline of the section of the blood vessel in a form of a contiguous pixel line in the at least one image provided from the relative spatial position of the side of the wall of the section of the blood vessel which delimits the flow channel and which faces the axis of symmetry;

derive the at least one geometric feature of the section of the blood vessel in the operating region from the adapted blood vessel model;

post-process the centerline by adapting connecting structures of pixels along the contiguous pixel line on a basis of pixel neighborhoods thereof;

decompose the post-processed centerline into a plurality of contiguous segments on a basis of a criterion; and, fit a corresponding parametric continuous function to each of the plurality of segments of the post-processed centerline by adapting function parameters such that an overall curve formed from the fitted parametric continuous functions is C1-continuous at each point.

20. A system for determining at least one geometric feature of a section of an object, wherein the object is a blood vessel in an operating region, the at least one feature being at least one of length, wall thickness, internal diameter and external diameter of a section of a blood vessel, the system comprising:

a device for providing at least one image of the section of the object;

a non-transitory computer readable storage medium; and a computer unit including a processor;

program code stored on said non-transitory computer readable storage medium;

said program code being configured, when executed by said processor, to:

provide at least one image of the section of the object;

determine an adapted blood vessel model for the section of the blood vessel by adapting a blood vessel model, which describes the section of the blood vessel as a flow channel with a wall delimiting the flow channel and with an axis of symmetry, via image processing using at least one of the images provided;

ascertain a relative spatial position of a side of the wall of the section of the blood vessel which delimits the flow channel and which faces the axis of symmetry in the at least one image provided;

determine a centerline of the section of the blood vessel in a form of a contiguous pixel line in the at least one image provided from the relative spatial position of the side of the wall of the section of the blood vessel which delimits the flow channel and which faces the axis of symmetry;

derive the at least one geometric feature of the section of the blood vessel in the operating region from the adapted blood vessel model;

post-process the centerline by adapting connecting structures of pixels along the contiguous pixel line on a basis of pixel neighborhoods thereof;

decompose the post-processed centerline into a plurality of contiguous segments on a basis of a criterion; and, fit a corresponding parametric continuous function to each of the plurality of segments of the post-processed centerline by adapting function parameters such that an overall curve formed from the fitted parametric continuous functions is C1-continuous at each point.

* * * * *

UNITED STATES PATENT AND TRADEMARK OFFICE
CERTIFICATE OF CORRECTION

PATENT NO. : 11,138,728 B2
APPLICATION NO. : 17/166945
DATED : October 5, 2021
INVENTOR(S) : Naber et al.

It is certified that error appears in the above-identified patent and that said Letters Patent is hereby corrected as shown below:

On the Title Page

On page 2:
Under "OTHER PUBLICATIONS", Line 16: delete B-Splines, and substitute -- B-Splines," -- therefor.
Under "OTHER PUBLICATIONS", Line 16: delete Vision", and substitute -- Vision -- therefor.

In the Specification

In Column 2:
Line 46: delete "by".

In Column 7:
Line 14: delete Wall-to-lumen and substitute -- "Wall-to-lumen -- therefor.

In Column 15:
Line 54: insert -- A -- before "Threshold".

In Column 18:
Line 51: delete Wall-to-lumen and substitute -- "Wall-to-lumen -- therefor.

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*